(12) United States Patent
Miyashita et al.

(10) Patent No.: US 9,907,716 B2
(45) Date of Patent: Mar. 6, 2018

(54) SLEEPING POSITION-CONTROLLING BED SYSTEM

(71) Applicant: TIZAI KEIEISHA CO., LTD., Osaka-shi, Osaka (JP)

(72) Inventors: Toshiko Miyashita, Osaka (JP); Kaname Ohmae, Osaka (JP)

(73) Assignee: TIZAI KEIEISHA CO., LTD, Osaka-shi (JP)

(*) Notice: Subject to any disclaimer, the term of this patent is extended or adjusted under 35 U.S.C. 154(b) by 0 days.

(21) Appl. No.: 15/589,407

(22) Filed: May 8, 2017

(65) Prior Publication Data

US 2017/0281439 A1 Oct. 5, 2017

Related U.S. Application Data

(63) Continuation of application No. 14/405,047, filed as application No. PCT/JP2013/072124 on Aug. 19, 2013, now Pat. No. 9,757,295.

(30) Foreign Application Priority Data

Aug. 18, 2012 (JP) .................... 2012-181260
Oct. 23, 2012 (JP) .................... 2012-234214

(51) Int. Cl.
*A61G 7/018* (2006.01)
*A61G 7/057* (2006.01)
(Continued)

(52) U.S. Cl.
CPC ............ *A61G 7/018* (2013.01); *A61B 5/1114* (2013.01); *A61B 5/4806* (2013.01); *A61G 7/001* (2013.01);
(Continued)

(58) Field of Classification Search
CPC ........ A61G 7/002; A61G 7/005; A61G 7/008; A61G 7/015; A61G 7/018; A61G 13/04; A61G 7/001; A61G 13/02
See application file for complete search history.

(56) References Cited

U.S. PATENT DOCUMENTS 3,041,122 A 6/1962 Weickgenannt
3,281,141 A 10/1966 Smiley
(Continued)

FOREIGN PATENT DOCUMENTS

JP 56-60508 A 5/1981
JP 2-125672 U 10/1990
(Continued)

OTHER PUBLICATIONS

International Search Report dated Sep. 10, 2013 issued in corresponding application No. PCT/JP2013/072124.
(Continued)

*Primary Examiner* — Eric J Kurilla
(74) *Attorney, Agent, or Firm* — Westerman, Hattori, Daniels & Adrian, LLP

(57) ABSTRACT

The sleeping-posture-control bed system includes a bed floor including a back-lifting portion for lifting the user's back, a bed-floor support body supporting the bed floor, and a back-lifting driver for lifting the head side of the back-lifting portion. The back-lifting portion includes a back-receiving surface and a head-receiving surface tiltable at different angles. The back-lifting driver lifts the back-receiving surface and the head-receiving surface, satisfying Mathematical Formula (1):

$$0°<\theta x \leq 70°, -45° \leq \theta y<0°, \text{ and } -30° \leq \theta x+\theta y \quad (1)$$

where θx is the tilt angle of the back-receiving surface when tilted, and the tilt angle of the back-receiving surface when the back-receiving surface is not lifted is
(Continued)

set to be 0°; and θy is the tilt angle of the head-receiving surface when the angle of an extended line of the back-receiving surface
at the tilt angle θx is referred to as 0°.

18 Claims, 23 Drawing Sheets

(51) Int. Cl.
    *A61G 7/015*     (2006.01)
    *G06K 9/00*     (2006.01)
    *A61G 7/00*     (2006.01)
    *A61B 5/11*     (2006.01)
    *A61B 5/00*     (2006.01)
    *A61G 7/005*     (2006.01)
    *A61G 7/008*     (2006.01)

(52) U.S. Cl.
    CPC ............. *A61G 7/005* (2013.01); *A61G 7/008* (2013.01); *A61G 7/015* (2013.01); *A61G 7/0573* (2013.01); *G06K 9/00228* (2013.01); *G06K 9/00369* (2013.01); *A61G 2203/30* (2013.01)

(56) References Cited

U.S. PATENT DOCUMENTS

| | | | |
|---|---|---|---|
| 3,584,321 A | 6/1971 | Buchanan |
| 3,635,461 A | 1/1972 | Bellucci |
| 3,754,749 A | 8/1973 | Lyon |
| D255,402 S | 6/1980 | Lundgren |
| 4,225,988 A | 10/1980 | Cary |
| 4,258,445 A | 3/1981 | Zur |
| 4,286,344 A | 9/1981 | Ikeda |
| 4,527,298 A | 7/1985 | Moulton |
| 4,882,797 A | 11/1989 | Failor |
| 6,691,348 B2 | 2/2004 | Plummer |
| 6,754,922 B2 | 6/2004 | Dewert |
| 6,961,971 B2 | 11/2005 | Schneider |
| 7,318,625 B2 | 1/2008 | Roither |
| 7,559,102 B1 | 7/2009 | Benzo |
| 8,683,629 B2 | 4/2014 | Clenet |
| 8,826,474 B2 | 9/2014 | Jackson |
| 2003/0221258 A1 | 12/2003 | Nagaoka et al. |
| 2004/0103475 A1 | 6/2004 | Ogawa et al. |
| 2004/0194213 A1 | 10/2004 | Weinman |
| 2008/0155750 A1 | 7/2008 | Mossbeck |
| 2009/0044339 A1 | 2/2009 | Morin |
| 2010/0071132 A1 | 3/2010 | Barthelt |
| 2010/0302044 A1 | 12/2010 | Chacon et al. |
| 2012/0159712 A1 | 6/2012 | Lee |
| 2012/0174316 A1 | 7/2012 | Shih |
| 2012/0198627 A1 | 8/2012 | Turner |
| 2013/0025066 A1 | 1/2013 | Shih |
| 2014/0039351 A1 | 2/2014 | Mix |
| 2014/0130254 A1* | 5/2014 | Jeong ................. A47D 9/02 5/109 |
| 2014/0237723 A1 | 8/2014 | Wysocki |
| 2014/0304915 A1 | 10/2014 | Lachenbruch |
| 2015/0136146 A1 | 5/2015 | Hood |
| 2015/0137835 A1 | 5/2015 | Chacon |

FOREIGN PATENT DOCUMENTS

| | | |
|---|---|---|
| JP | 7-289592 A | 11/1995 |
| JP | 2004-8466 A | 1/2004 |
| JP | 2004-16387 A | 1/2004 |
| JP | 2004-121837 A | 4/2004 |
| JP | 2005-168554 A | 6/2005 |
| JP | 2005-230511 A | 9/2005 |
| JP | 2005-270627 A | 10/2005 |
| JP | 2006-51212 A | 2/2006 |
| JP | 3862668 B2 | 12/2006 |
| JP | 2007-222462 A | 9/2007 |
| JP | 2007-222463 A | 9/2007 |
| JP | 2008-107258 A | 5/2008 |
| JP | 2008-131974 A | 6/2008 |

OTHER PUBLICATIONS

Office Action dated Jul. 11, 2017, issued in counterpart Japanese Application No. 2015-202722, with English translation (9 pages).

* cited by examiner

SLEEPING POSITION-CONTROLLING BED SYSTEM

CROSS REFERENCE TO RELATED APPLICATION

The present invention is a Divisional application of U.S. patent application Ser. No. 14/405,047, filed on Dec. 2, 2014, which is a National Stage Application filed under 35 USC '371 of International Application No. PCT/JP2013/072124, filed Aug. 19, 2013, and which is based upon and claims the benefit of priority from the subject matter related to Japanese Patent Application No. 2012-181260 filed on Aug. 18, 2012, and Japanese Patent Application No. 2012-234214 filed on Oct. 23, 2012 in the Japan Patent Office, the entire contents of which are hereby incorporated by reference.

TECHNICAL FIELD

The present invention relates to a bed system controlling a user's sleeping posture.

BACKGROUND ART

Many bedridden patients cannot turn over in bed and have blood circulation disorders with the risk of developing pressure ulcers (also called "bed sores"). Pressure ulcers deteriorate the health status of patients sometimes crucially. To avoid this problem, home caregivers need to help to change patients posture about every two hours, which is a heavy burden for the home caregivers.

Meanwhile, in today's stressful society, more and more people are unconsciously suffering from sleep disorders such as sleep apnea syndrome, snoring, and teeth grinding. A severe form of sleep apnea syndrome is a life-threatening disease, and even a milder form of it reduces the quality of sleep, possibly causing affected people to fall asleep on duty. For example, if pilots and drivers of trains and buses are affected with sleep disorders, they may cause a catastrophic accident involving human lives. For these people to lead a normal social life, it has been hoped to develop measures for easily preventing or reducing sleep disorders of which people are unaware themselves, such as sleep apnea syndrome, snoring, and teeth grinding.

Patent Literatures 1 and 2 have proposed care bed techniques which help a patient to change his/her posture in bed. In Patent Literature 1, the bed is automatically rotated along the circumference of a circular slider so as to turn over a patient in bed.

In Patent Literature 2, the bed includes a bottom board having a lower surface from which a semicircular body protrudes so as to form a semicircular orbit in the width direction of the bed; and a bed frame which holds the bottom board in a tiltable manner while supporting the semicircular body so as to rotate it in a half circle along its circumference. When the bottom board is driven, the semicircular body rotates in a half circle along the semicircular orbit, allowing a bottom surface of the bottom board to tilt in the width direction of the bed.

CITATION LIST

Patent Literatures

Patent Literature 1: Japanese Unexamined Patent Publication No. 2005-168554

Patent Literature 2: Japanese Unexamined Patent Publication No. 2004-16387

According to the techniques of Patent Literatures 1 and 2, the beds are tilted by caregivers to help patients to change their posture in bed.

SUMMARY OF THE INVENTION

Problems to be Resolved by the Invention

Patients and aged people who are bedridden often cannot change their posture in bed by themselves. Therefore, they are likely to have blood circulation disorders at a contact area between the body and the surface of the bed that supports the body and then to suffer from pressure ulcers. Meanwhile, those who suffer from sleep apnea syndrome causing the cessation of breathing or hypopnea, snoring, or teeth grinding are in a state of chronic sleep deprivation due to a continuous lack of quality sleep and may even die suddenly.

Furthermore, those who suffer from low-back pain and shoulder pain, and patients who have just undergone surgery are often unable to fall asleep unless they are in a comfortable posture. Even if they get to sleep, they may involuntary change their posture during sleep and be woken up by a sudden pain.

Chronic sleep deprivation due to these causes may prevent affected people from having a healthy life, and possibly cause a catastrophic accident involving human lives. Nevertheless, most of these people are unaware of having such sleep disorders themselves.

An object of the present invention is to provide a bed system capable of being tilted in multiple directions. The bed system can tilt its bottom surface regularly, discontinuously, or whenever necessary to prevent a bedridden patient from developing pressure ulcers. The bed system can also detect the user's parasomnias such as apnea, hypopnea, snoring, and teeth grinding, and upon detection of a parasomnia, induce the user to change his/her sleeping posture so as to reduce the parasomnia.

To achieve the above object, the present invention has the following aspects.

(1) First Aspect

A sleeping-posture-control bed system includes: a bed floor including a back-lifting portion for lifting the user's back; a bed-floor support body supporting the bed floor; and a back-lifting driver for lilting the head side of the back-lifting portion to tilt the back-lifting portion, wherein the back-lifting portion includes a back-receiving surface and a head-receiving surface tiltable at different angles; and the back-lifting driver lifts the back-receiving surface and the head-receiving surface so as to satisfy Mathematical Formula (1):

$$0° < \theta x \leq 70°, -45° \leq \theta y < 0°, \text{ and } -30° \leq \theta x + \theta y \quad (1)$$

where $\theta x$ is the tilt angle of the back-receiving surface when tilted, and the tilt angle of the back-receiving surface when the back-receiving surface is not lifted is set to be 0°; and $\theta y$ is the tilt angle of the head-receiving surface when the angle of an extended line of the back-receiving surface at the tilt angle $\theta x$ is referred to as 0°.

In the first aspect, the tilt angle $\theta x$ is an angle of elevation (positive angle) of the back-receiving surface with reference to the tilt angle 0° at which the back-receiving surface is not lifted, whereas the tilt angle $\theta y$ is a negative angle of elevation (positive angle of depression) when the angle of an extended line of the back-receiving surface at the tilt angle θx is referred to as 0°.

In the range 0°<θx≤70°, the user's head is held higher than the low-back of the body when he/she is lying supine on the sleeping-posture-control bed system. In addition, in the range −45°≤θy<0°, the user's head changes from the state of being thrown back up to a maximum angle of 45° to substantially the same angle as his/her back. Furthermore, in the range of −30°≤θx+θy, the angle of elevation of the user's head with respect to the back-receiving surface that is not lifted is up to a maximum of −30°. Thus, the tilt of the head with respect to the horizontal surface is up to a maximum of −30°, provided that the bed floor of the sleeping-posture-control bed of the present invention is placed perpendicular to the direction of gravity (parallel to the horizontal surface).

Assume, for example, that the user's head is thrown back 10° with respect to the center line passing through the head and the body (the angle of elevation θy is −10°) in order to widen his/her airway. In this case, even if the user's head remains horizontal, the head can be thrown back 10° with respect to the center line passing through the head and the body by tilting the back-receiving surface at an angle of 10°. As a result, the user's airway is widened. Thus, this posture allows the user's airway to be widened without putting a load on his/her heart or rushing too much blood to his/her head.

(2) Second Aspect

In the sleeping-posture-control bed system of the first aspect, the back-lifting driver lifts the back-receiving surface and the head-receiving surface so as to satisfy Mathematical Formula (2):

$$0°<\theta x \leq 70°, -45° \leq \theta y<0°, \text{ and } 0° \leq \theta x+\theta y \quad (2)$$

(3) Third Aspect

A sleeping-posture-control bed system includes: a bed floor including a back-lifting portion for lifting the user's back; a bed-floor support body supporting the bed floor; and a back-lifting driver for lilting the head side of the back-lifting portion to tilt the back-lifting portion, wherein the back-lifting portion includes a back-receiving surface and a head-receiving surface tiltable at different angles; and the back-lifting driver lifts the back-receiving surface and the head-receiving surface so as to satisfy Mathematical Formula (3):

$$2° \leq \theta x \leq 85°, -45° \leq \theta y \leq -2°, \text{ and } 0° \leq \theta x+\theta y \quad (3)$$

where θx is the tilt angle of the back-receiving surface when tilted, and the tilt angle of the back-receiving surface when back-receiving surface is not lifted is set to be 0°; and θy is the tilt angle of the head-receiving surface when the angle of an extended line of the back-receiving surface at the tilt angle θx is referred to as 0°.

In the third aspect, the head-receiving surface is made tilted down by not more than 2° (−2° as the angle of elevation) with respect to the back-receiving surface, while the angle of the head-receiving surface (angle of elevation) with respect to the horizontal surface (perpendicular to the vertical line) is made not less than 0°. In other words, in the third aspect, the user's head can be tilted down at not less than 2° with respect to the human body center line passing through the body by tilting the back-receiving surface by 2° or more while maintaining the condition that the head is not made lower than the horizontal surface. The lower limit of θx only needs to be not less than 2°, but in order to increase the effect of widening the airway, it can be not less than 3°, 5°, 7°, or 10°.

(4) Fourth Aspect

In the sleeping-posture-control bed system of the first aspect, the bed-floor support body includes a bed-floor tilt driver for tilting the bed floor.

Bedridden patients and the like cannot change their posture in bed by themselves or can have a very few number of body movements. The bedridden patients have the risk of developing pressure ulcers (bed sores) at a certain body part when it is compressed for a long time. To avoid pressure ulcers, the patients need to be changed in their posture regularly (for example, about every two hours). In the fourth aspect, the user's center of gravity can be changed by tilting the bed floor so as to induce the user to turn over downward, thereby preventing pressure ulcers.

Furthermore, in the fourth aspect, the user's body is bent into an inverted "V" shape at his/her neck with the head down by bending the back- and head-receiving surfaces. In addition, the bed-floor tilt driver is driven to tilt the bed floor so that the user's face can be up. For example, when the user lying on his/her side has a hypopnea or is snoring, these problems can be eliminated by inducing the user to turn his/her face up and to be bent into an inverted "V" shape at his/her neck, thereby directly widening his/her airway.

(5) Fifth Aspect

The sleeping-posture-control bed system of any one of the first to fourth aspects further includes: a sleep monitor for monitoring sleep of the user sleeping on the bed floor; a parasomnia detector for detecting the presence or absence of parasomnias on the basis of monitoring data of the sleep monitor; and a back-lifting tilt controller for determining the θx and θy on the basis of the determination result of the parasomnia detector and for driving the back-lifting driver so as to satisfy the determined conditions.

People cannot know their sleeping conditions such as the presence of sleep apnea, snoring, and teeth grinding. The bedridden patients and the like have a very small number of body movements, which they cannot improve themselves. Those with chronic low-back pain or stiff shoulders and those who have just undergone surgery are awakened by a sudden pain when unconsciously changing their posture in bed. In the fifth aspect, however, the sleep monitor, the parasomnia detector, the tilt driving controller, and the back-lifting driver and/or the bed-floor tilt driver act in cooperation with each other to improve the quality of sleep of the user regularly, intermittently, or arbitrarily.

The following is a description of technical and medical significance of the sleeping-posture-control bed system described above. Apnea and hypopnea are mainly caused when the tongue root or the soft palate is lowered due to muscle relaxation during sleep and closes the airway. The airway is likely to be closed by the tongue root or the soft palate especially when people are lying supine, thereby causing apnea or hypopnea. In contrast, when people are lying on their side, their airway is unlikely to be closed by the tongue root or the soft palate. Therefore, sleep apnea or hypopnea may be reduced by making people lying on their side, or throwing their head back when sleep apnea or hypopnea appears.

Snoring is caused when the tongue root or the soft palate is lowered due to muscle relaxation during sleep and partially closes the airway. Therefore, snoring can be often reduced in the same manner as the case of sleep apnea when snoring appears. Teeth grinding, on the other hand, is often caused when people are lying on their side or with their face down, and is unlikely to be caused when they are lying with their face up. Therefore, it is often the case that teeth grinding can be reduced by making people lie supine when teeth grinding appears. When people have both teeth grinding and snoring, it is often the case that both can be reduced by making them lie supine and throwing their head back.

In the fifth aspect, the sleep monitor monitors the user, and the parasomnia detector determines the presence or absence of parasomnias (such as apnea, hypopnea, snoring, and teeth grinding). If the parasomnia detector detects the presence of parasomnia, the back-lifting tilt controller controls the back-lifting driver on the basis of the information so as to lift the back-receiving surface and the head-receiving surface or to tilt the bed floor under Mathematical Formulas (1) to (3). This can widen the airway of the user lying on the bed floor or induce the user to change his/her posture into a posture unlikely to cause parasomnias.

(6) Sixth Aspect

The sleeping-posture-control bed system of the fourth aspect further includes: a sleep monitor for monitoring sleep of the user sleeping on the bed floor; a parasomnia detector for detecting the presence or absence of parasomnias on the basis of monitoring data of the sleep monitor; and a back-lifting tilt controller for determining the $\theta x$ and $\theta y$ on the basis of the determination result of the parasomnia detector and for driving the back-lifting driver so as to satisfy the determined conditions, wherein on the basis of the determination result of the parasomnia detector, the back-lifting tilt controller determines the tilt direction and angle of the bed floor as well as the $\theta x$ and $\theta y$, and then drives the back-lifting driver and/or the bed-floor tilt driver so as to satisfy each of the determined conditions.

In the sixth aspect, the back-lifting tilt controller drives the back-lifting driver and the bed-floor tilt driver on the basis of information from the parasomnia detector so that the lifting of the back-lifting portion and the tilting of the bed floor in the lateral or longitudinal direction can act together on the user. This allows these drivers to be driven more sensitively depending on the clinical condition of the user. For example, the back-receiving surface and head-receiving surface are moderately lifted and tilted (for example, at an angle of 2° to 15°, or 3° to 30°), so that the back and head of the user can be bent into an inverted "V" shape at his/her neck. Next, the bed floor is tilted either to the right or left at, for example, 2° to 8°, and preferably 2.5° to 5°, thereby inducing his/her face to be up. As a result, the user's parasomnias can be reduced without disturbing the user's sleep or bringing discomfort or burden to the user.

(7) Seventh Aspect

The sleeping-posture-control bed system of any one of the first to sixth aspects further includes a head detector for detecting whether the user's head is located on the head-receiving surface or not.

When the user's head is not on the head-receiving surface, tilting the head-receiving surface does not have the effect of widening the airway. Therefore, it is essential to determine whether the user's head is on the head-receiving surface or not. To achieve this, it is preferable to display the detection results of the head detector on a display screen or to sound a warning beeper when the user's head is not on the head-receiving surface, thereby correcting the user's sleeping posture. When the user's head is not on the head-receiving surface, it is alternatively preferable that the back-lifting tilt controller be configured to drive the back-lifting driver so as to make the tilt angle of the head-receiving surface equal to that of the back-receiving surface ($\theta y=0°$).

(8) Eighth Aspect

The sleeping-posture-control bed system of any one of the first to seventh aspects further includes a face direction detector for detecting whether the user's face is up, tilted to the right, tilted to the left, or down with respect to the head-receiving surface.

As described above, the types of parasomnias are closely related to whether the user is lying supine or on his/her side. It is necessary to determine the tilt direction of the bed floor depending on the user's sleeping posture, or not to tilt the head-receiving surface when the user is not lying supine. Since the face direction clearly shows the sleeping posture, the bed system can be appropriately controlled by finding the user's face direction with respect to the head-receiving surface (up, tilted to the right, tilted to the left, down).

Thus, it is preferable that the back-lifting tilt controller be configured to drive the back-lifting driver and the bed-floor tilt driver on the basis of the information from the face direction detector. For example, when the user's face is tilted to the right, the bed floor is tilted to lower the user's left shoulder. This induces the user to be supine or to be tilted to the left.

The head detector or the face direction detector can be formed of a pressure sensing sheet with a grid pattern composed of a plurality of sections. This sheet is placed on the head-receiving surface to detect the pressure distribution. As a result, the presence and direction of the head on the surface can be determined from the shape of the pressure distribution pattern.

(9) Ninth Aspect

The sleeping-posture-control bed system of the fifth or sixth aspect further includes: a head detector for detecting whether the user's head is located on the head-receiving surface or not; and a face direction detector for detecting whether the user's face is up, tilted to the right, tilted to the left, or down with respect to the head-receiving surface, wherein the head detector further has the head position detecting function of detecting in which region of the head-receiving surface the user's head is located, and the back-lifting tilt controller determines the tilt angle of the head-receiving surface and the tilt direction of the bed floor on the basis of head position information obtained from the head detector and face direction information obtained from the face direction detector, and then drives the back-lifting driver and/or the bed-floor tilt driver.

Particular effects of the present invention are unlikely to be obtained if the back-lifting driver and the bed-floor tilt driver are driven when the user's head is not on the head-receiving surface due to his/her unbalanced posture on the bed floor. In the ninth aspect, however, the back-lifting driver and/or the bed-floor tilt driver can be properly driven to obtain the particular effects of the present invention.

Assume, for example, when the user's head is on the right side of the head-receiving surface due to his/her unbalanced posture on the bed floor. In this case, if the bed floor is tilted to the right, the user's head may go outside the head-receiving surface. Therefore, tilting to the right is restricted. When the head is protruding toward the head frame (the side far from the back-receiving surface), if [$\theta x+\theta y$] has a large negative value (for example, over −10° or over −20°), the user's neck is subjected to a large stress, which can result in neck sprain or other injury. Furthermore, if the bed floor is tilted in the longitudinal direction to lower the head when the head is protruding toward the head frame, the head may protrude in the longitudinal direction of the bed. Therefore, in such a case, it is preferable to restrict the tilting to lower the head.

In order to be detected by the head detector, the head-receiving surface can be divided into three regions: "right", "center", and "left" (divided in the lateral direction of the bed floor), or "top", "center", and "bottom" (divided in the longitudinal direction of the bed floor). Alternatively, the head-receiving surface can be divided into nine regions, that is, three regions 1 to 3 in each of the left, center, and right (for example, 3 represents the lower side, and 1 represents the upper side). In this case, when the center of gravity of the user's head is located in the "center 2" including the center of the area, the user is in an optimum sleeping posture.

(10) Tenth Aspect

A sleeping-posture-control bed system includes: a bed body including a bottom surface; a bed-floor tilt driver for tilting the bottom surface; a sleep monitor for monitoring sleep of the user sleeping on the bottom surface; a parasomnia detector for detecting the presence or absence of parasomnias on the basis of monitoring data of the sleep monitor; and a tilt driving controller for controlling the bed-floor tilt driver on the basis of the determination result of the parasomnia detector so that the bottom surface is tilted.

The tenth aspect is substantially identical to the sixth aspect except for not including the back-lifting portion. The tenth aspect has substantially the same effect as the fourth and sixth aspects except for the effect of widening the airway by means of the back-lifting portion.

The bed body of the tenth aspect can employ a well-known suspended structure (Japanese Unexamined Patent Publication No. 2009-89860) or other well-known framework structure. The structure of the bed-floor tilt driver is not particularly limited. For example, the driver can be composed of a driving means for tilting the bottom surface by means of a hydraulic pressure or a motor, and a holding means for holding the tilt by means of a hydraulic pressure or a stopper (locking member).

The sleep monitor monitors and detects at least one of the following monitoring elements, which are indicators of parasomnias, and the face direction of the user lying. Examples of the monitoring elements include heart rate, blood pressure, body temperature, body surface temperature, brain waves, blood oxygen levels, the number of body movements, changes in body posture, the amount of $CO_2$ in the atmosphere around the user, the gas flow rate around the mouth and nose of the user, snoring sound, and teeth-grinding sound. In order to detect these monitoring elements, the sleep monitor can include the following: a monitoring camera for monitoring the face direction of the user lying, a pressure-sensitive sheet placed on the portion of the bottom surface on which the user's head is positioned, or on a mattress pad or a mattress covering the portion, or on a pillow, or a triaxial sensor attached to the user's head; and a sensor for monitoring some monitoring elements, which are indicators of parasomnias, the sensor including an overnight polysomnography, a brain wave sensor, a biosensor for measuring and recording electrocardiogram/heartbeat/body surface temperature/triaxial acceleration of the trunk of the body in real time; a pulse oximeter for monitoring pulse rate and saturation of pulse oximetry oxygen ($SpO_2$), a sheet-like multipoint pressure sensor for monitoring body movements, a radio frequency sensor for body movements, a monitoring camera, an air-flow sensor, a gas component sensor, a sound sensor, and a vibration sensor.

The parasomnia detector includes a processing unit such as a central processing unit, and a storage device. The parasomnia detector determine the presence or absence of parasomnias and/or the types of parasomnias by comparing information obtained from the sleep monitor and criteria information stored in the storage device. The types of the parasomnias include apnea, hypopnea, snoring, teeth grinding, abnormal body movement (too many or too few), abnormal body temperature (too low or too high), abnormal blood pressure (too high or too low), and abnormal heart rate (too high or too low). The criteria information is reference information determined by the relationship with the above-mentioned monitoring elements, such as an average person's heart rate, the number of body movements per unit time, body surface temperature, and blood oxygen levels. The storage device only needs to be accessible from the processing unit via a wired or wireless circuit and does not need to be present near the bed. Meanwhile, the processing unit only needs to be configured to acquire monitoring information of the sleep monitor and to perform a determination process, and does not need to be present near the bed.

The tilt driving controller determines the user's face direction from the monitoring information of the sleep monitor, and controls the bed-floor tilt driver on the basis of this determination information and the determination result of the parasomnia detector so that the bottom surface can be tilted. To achieve these functions, the tilt driving controller includes a processing unit such as a central processing unit, and a storage device for storing the information to determine the user's face direction and software information to control the bed-floor tilt driver. The tilt driving controller determines the face direction by comparing the information to determine the face direction stored in the storage device of the tilt driving controller with the monitoring information of the sleep monitor. The software information is software information for which the bed needs to be tilted in a direction to allow the bed-floor tilt driver to reduce apnea (to induce the user to a lateral sleeping posture) when the determination result of the parasomnia detector is apnea.

When the user lying on his/her side, not lying supine, is detected to have apnea or hypopnea, first of all, the user is induced to a different posture (lying supine or lying on his/her other side), and then the apnea or hypopnea is monitored. If the apnea or hypopnea is not reduced, the user is induced to a different posture. If the user's apnea or hypopnea is still not reduced (the presence of apnea or hypopnea is detected) even in the different posture, a beeper can be sounded to wake up the user. Thus, the tilting procedure can be made arbitrarily, and can be achieved by making the storage device of the tilt driving controller store software information to drive the bed-floor tilt driver. In the same manner, an appropriate procedure can be made also for teeth grinding or snoring, and software information for tilting can be stored in the storage device of the tilt driving controller.

Similar to the parasomnia detector, the storage device only needs to be accessible from the processing unit via a wired or wireless circuit. Furthermore, the processing unit of the parasomnia detector may also serve as the processing unit of the tilt driving controller, and the storage device of the parasomnia detector may also serve as the storage device of the tilt driving controller. The tenth aspect may be provided with a display screen, a red light, or a beeper. When the parasomnia detector determines that the user has a small number of body movements, this is informed by showing a message on the display screen, lighting up the red light, or sounding the beeper, so that the caregiver can arbitrarily tilt the bed bottom surface.

(11) Eleventh Aspect

The sleeping-posture-control bed system of the tenth aspect further includes a barycentric position detector for detecting the user's center of gravity, wherein the tilt driving controller controls the bed-floor tilt driver so that when the parasomnia detector has detected the presence of parasomnias, the position of the user's center of gravity on the bottom surface is made located higher in the tilt direction than the center line of the tilted bottom surface, the center line being perpendicular to the tilt direction of the bottom surface and including the center point of the area of the bottom surface.

The barycentric position detector can be achieved by installing a gravity sensor or a multipoint pressure sensor on the bed body or on a bed mat placed on the bed body. It can alternatively be achieved by providing an image capture device above the bed, and calculating the center of gravity through image analysis. The provision of the barycentric position detector can prevent the user from falling off the bed due to a change in his/her posture.

(12) Twelfth Aspect

In the sleeping-posture-control bed system of the eleventh aspect, if the position of the user's center of gravity after the bottom surface is tilted is moved above a threshold with reference to the position of the user's center of gravity when a parasomnia is detected, the tilt driving controller controls the bed-floor tilt driver so as to reduce the tilt of the bottom surface.

Assume that the tilting of the bottom surface has caused the user's center of gravity to move over the threshold with reference to the user's center of gravity when the presence of parasomnia is determined. In this case, if the tilt angle of the bed bottom surface is maintained or increased, the user may fall off the bed or have other troubles. In contrast, in the twelfth aspect, when the user's center of gravity moves over the threshold, the tilt of the bed bottom surface is reduced so as to prevent the user from falling off the bed or having other troubles. The above-mentioned threshold is determined in consideration of the user's physical strength and clinical condition, the size of the bed bottom area, characteristics of the mat (smoothness of texture, compression-rebound characteristics, compression ratio) etc.

(13) Thirteenth Aspect

In the sleeping-posture-control bed system of the tenth aspect, the bottom surface is configured to be tilted around a first axis of tilt corresponding to a direction opposite to the longitudinal direction of the bed body, and also to be tilted around a second axis of tilt perpendicular to the first axis of tilt.

The user generally lies supine with his/her head on one side and legs on the other side in the longitudinal direction of the bed. Therefore, the position of the user's center of gravity with respect to the bottom surface can be changed by tilting the bottom surface about the first axis of tilt. For example, the user's posture can be changed from supine to side lying. In this case, it is made easy to change the position of the user's center of gravity or posture in bed by tilting the bed bottom surface in lateral and longitudinal directions, for example, about both the second axis of tilt and the first axis of tilt. Tilting the bed bottom surface about the second axis of tilt allows the user to raise upper body and to take a meal. The phrase "the direction opposite to the longitudinal direction of the bed body" means the direction of a line segment connecting an arbitrary point on one side (the head side) and an arbitrary point on the other side (the foot side) of the rectangular bottom surface. Consequently, the first axis of tilt is not necessarily parallel to the center line (the longitudinal center line) which laterally divides the area of the bed bottom surface into two equal parts. It is, of course, possible to make the first axis of tilt agree with the longitudinal center line.

(14) Fourteenth Aspect

The sleeping-posture-control bed system of the thirteenth aspect further includes a barycentric position detector for detecting the user's center of gravity, wherein if the position of the user's center of gravity after the bottom surface is tilted is moved above a threshold with reference to the position of the user's center of gravity when a parasomnia is detected, the tilt driving controller controls the bed-floor tilt driver so as to reduce the tilt of the bottom surface.

In the fourteenth aspect, the bed-floor tilt driver can be properly controlled in relation to the position of the user's center of gravity and the threshold. If the bed bottom is kept tilted or tiled further even after the user has changed his/her posture, the user may become unstable in posture and may fall off the bed. In the fourteenth aspect, however, the tilt of the bed bottom surface can be properly controlled to prevent such problems.

The barycentric position detector for detecting the user's center of gravity can include, for example, a center-of-gravity sensor, a multipoint pressure sensor, a radio frequency sensor for body movements, and a monitoring camera. In the case of employing a multipoint pressure sensor, the point at which the highest pressure is detected is determined to be the center of gravity. In the case of employing a monitoring camera, the center of gravity can be determined through image analysis.

(15) Fifteenth Aspect

The sleeping-posture-control bed system of any one of the tenth to fourteenth aspects further includes a bed mat to be placed on the bottom surface, the bed mat having a recess formed from both ends of the mat in the width direction thereof toward the center along the longitudinal direction of the bed.

In the fifteenth aspect, the bed mat, which is placed on the bottom surface, has a depressed portion extending from both ends in the width direction of the mat toward the center along the longitudinal direction of the bed. In the bed mat in this shape, when the bed bottom surface is tilted in the lateral direction perpendicular to the longitudinal direction, both ends of the bed mat having the depressed portion prevent the user from slipping down the bed mat. Both ends in the width direction of the mat means the opposite long sides in the case that the mat has four sides.

(16) Sixteenth Aspect

In the sleeping-posture-control bed system of the fifteenth aspect, the recess of the bed mat is elliptic arc in a cross section perpendicular to the longitudinal direction of the bed.

When the depressed portion has an elliptic arc cross section, the curvature gradually increases from the bottom of the depressed portion toward the right and left ends of the mat. This prevents the user from feeling uncomfortable and from slipping down the bed mat when the bed bottom surface is tilted in the lateral direction perpendicular to the longitudinal direction. Furthermore, when the depressed portion has an elliptic arc cross section, the user can be changed in his/her posture by tilting in the lateral direction.

(17) Seventeenth Aspect

The sleeping-posture-control bed system of any one of the tenth to fourteenth aspects further includes a bed mat to be placed on the bottom surface, the bed mat having a higher compressibility in the center thereof than in both ends thereof.

In the seventeenth aspect, when the user lies on the bed mat, the central portion of the bed mat sinks deeper to hold the user, preventing the user from slipping down the bed mat when the bed bottom surface is tilted laterally. In the seventeenth aspect, the bed mat may be configured to have a depressed portion, and the depressed portion may be configured to have an elliptic arc cross section.

Advantageous Effect of the Invention

The present invention provides a sleeping-posture-control bed system which can control the user's sleeping posture automatically or arbitrarily depending on the user's body condition. The present invention further provides a sleeping-posture-control bed system which can automatically monitor body movements or abnormal behaviors of the user during sleep, and upon detection of a parasomnia, can automatically lift the back- and head-receiving surfaces and/or tilt the bed floor.

The bed system of the present invention helps users incapable of turning over by themselves to change their posture in bed or to shift their center of gravity. This prevents bedridden people from developing pressure ulcers (bed sores), or eliminates or reduces their parasomnias such as apnea, hypopnea, snoring, and teeth grinding. The bed system of the present invention can allow people with pain whose intensity varies depending on their sleeping posture to be kept in a comfortable posture during sleep. These people include those who have just undergone surgery, those with stiff shoulders due to age or low-back pain, and those with pain in one side of the body or in one arm.

Thus, the present invention has the effect of improving the quality of sleep of people with various sleep disorders and also allowing patients with heart problems to be kept in a posture in which the load on the heart is low.

BRIEF DESCRIPTION OF DRAWINGS

FIG. 25(1) is a sectional view of the internal structure of a back-receiving-surface longitudinal main member; FIG. 25(2) is a sectional view of the internal structure of a back-receiving-surface longitudinal elastic member; and FIG. 25(3) shows the back-receiving-surface longitudinal main member and the back-receiving-surface longitudinal elastic member which is screwed in the back-receiving-surface longitudinal main member.

DESCRIPTION OF EMBODIMENTS

Embodiments of the present invention will now be described with reference to the accompanying drawings.

First Embodiment

Figure 1:
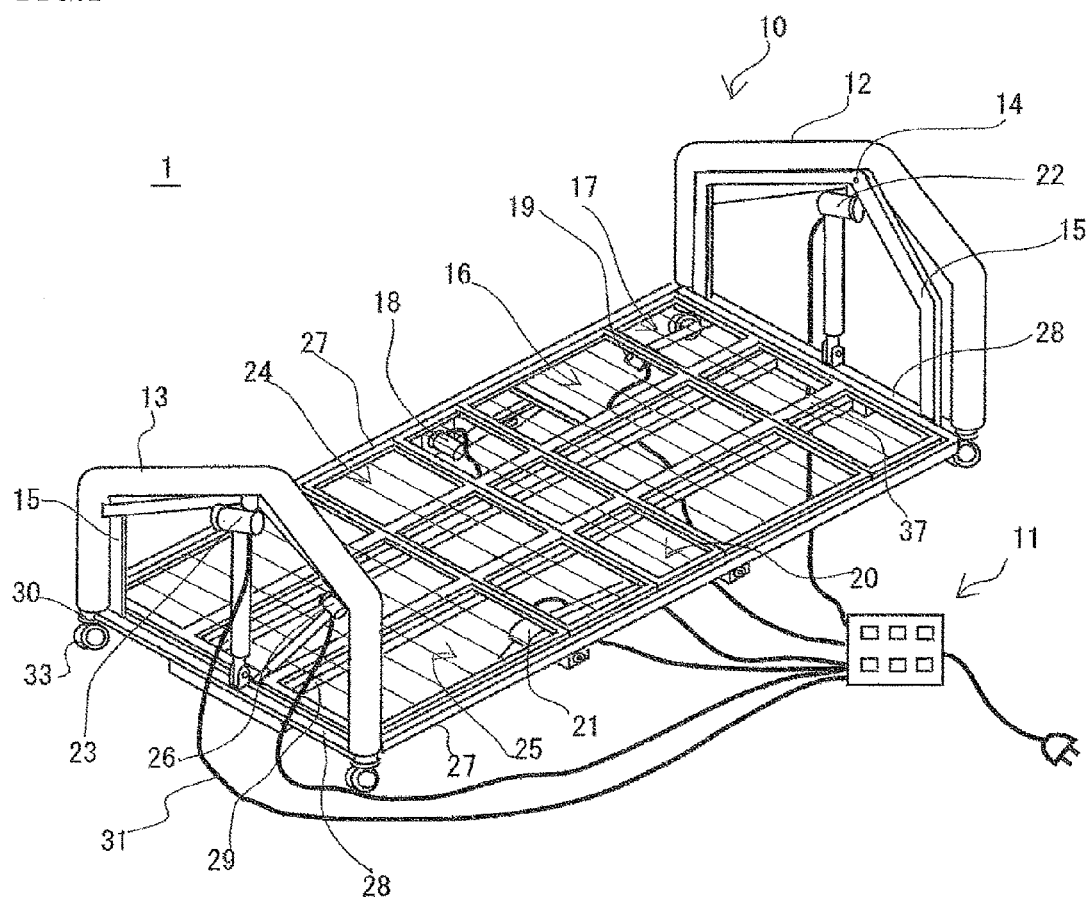
FIG. 1 is a perspective view of a sleeping-posture-control bed system of a first embodiment when a bed floor is in a flat position.

FIG. 1 shows a sleeping-posture-control bed system 1 of a first embodiment of the present invention, which includes a bed body 10 and an operating unit 11. The bed body 10 includes a bed floor on which the user lies, and a bed-floor support body which supports the bed floor. The bed floor mainly includes two lateral frame members 28, two longitudinal frame members 27 each connecting one end of each of the lateral frame members 28, and two connecting members 37 disposed between the longitudinal frame members 27 so as to connect the lateral frame members. This framework is suspended by two suspension members 15 fixed to reinforcing members 32 of a head frame 12 and a foot frame 13. The framework forms the upper surface of the bed floor, which is hereinafter also referred to as the "bottom surface" on or over which the user lies.

Figure 2:
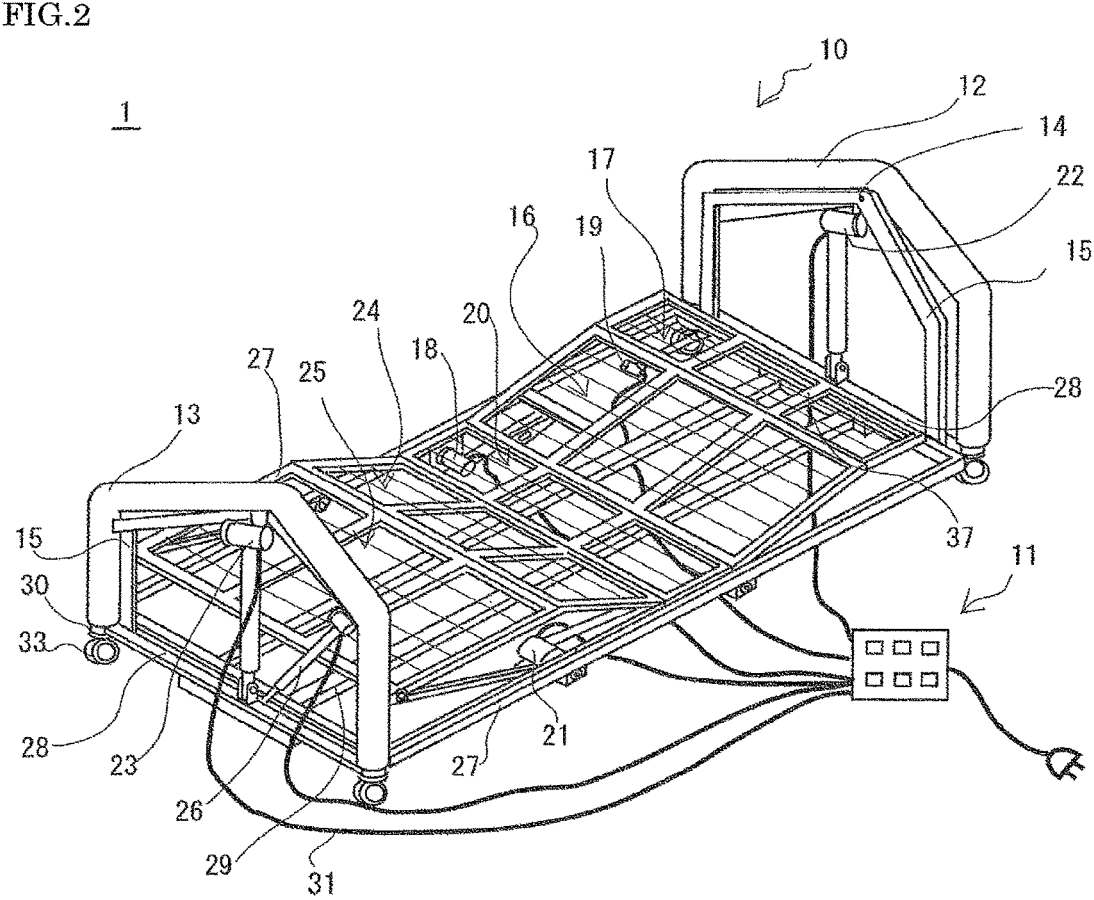
FIG. 2 is a perspective view of a bed body in the first embodiment when a back-receiving surface portion, a head-receiving surface portion, an upper-leg-receiving surface portion, and a lower-leg-receiving surface portion are in a raised position.

The bed floor includes a head-receiving surface portion 17, a back-receiving surface portion 16, a waist-receiving surface portion 20, an upper-leg-receiving surface portion 24, and a lower-leg-receiving surface portion 25 (see FIG. 2). Adjacent ones of these receiving surfaces are rotatably coupled to each other. The bed system further includes a driver for the head-receiving surface (actuator 19), which lifts the head-receiving surface portion 17; a driver for the back-receiving surface (actuator 18), which lifts the back-receiving surface portion 16; and a knee bending driver (actuator 21), which lifts the upper-leg-receiving surface portion 24 and the lower-leg-receiving surface portion 25. These drivers are disposed in proper locations inside the longitudinal frame members 27.

Figure 5:
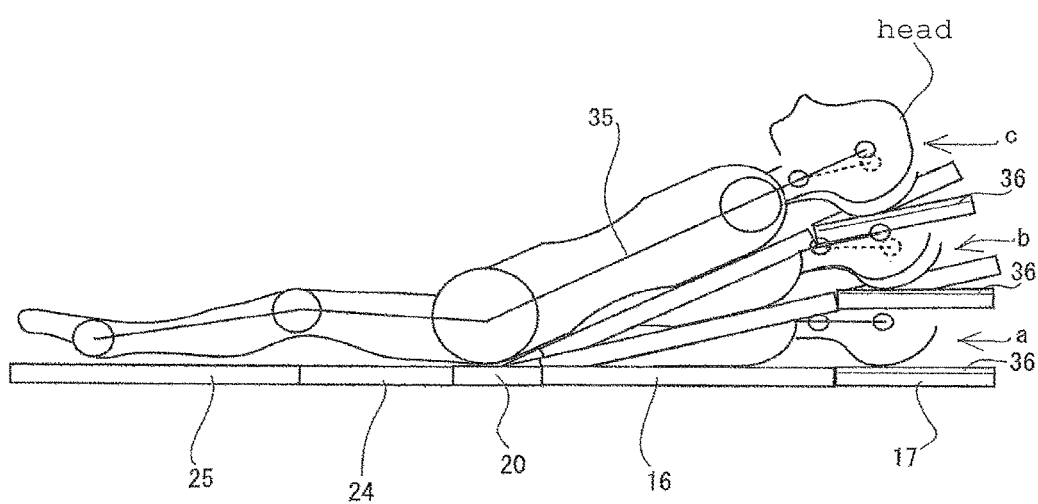
FIG. 5 is an explanatory drawing showing the tilts of the back-receiving surface portion and the head-receiving surface portion of the bed floor and the up and down movements of the user's head.

As shown in FIG. 5, the head-receiving surface portion 17 has a pressure-sensitive sheet 36 thereon as a face direction detector, which also serves as a head detector. The sheet is a pressure sensing sheet with a grid pattern composed of a plurality of sections. Each section is supplied with current when a load is applied thereto. The current is in proportion to the magnitude of the load in order to show a pressure distribution pattern. The operating unit 11 includes a storage unit which stores information for detecting the head position and information for detecting the face direction (a pattern for detecting the face direction). The presence or absence and position of the user's head on the sheet 36 and the face direction can be detected by comparing the shape of the detected pressure distribution pattern with the information stored in the storage unit of the operating unit 11.

Figure 3A:
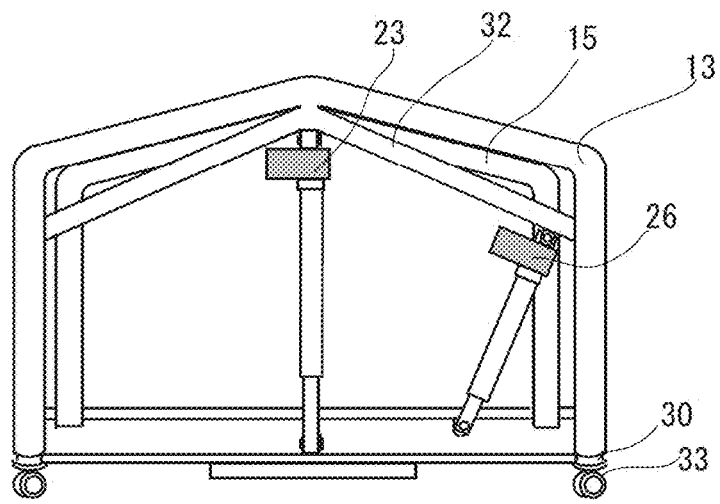
FIG. 3(a) is a front view of the bed body in the first embodiment as seen from a foot frame.
Figure 3B:
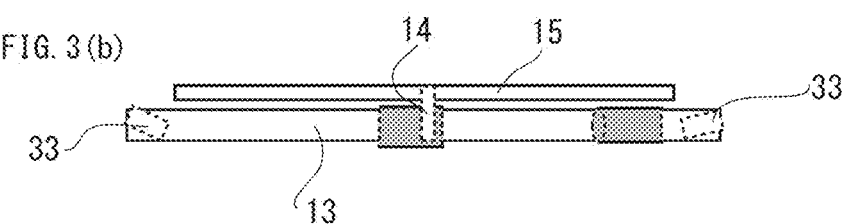
FIG. 3(b) is a partial plan view of a foot frame as seen from above.

The bed-floor support body which supports the bed floor includes the head frame 12 and the foot frame 13, which are inverted U-shaped and have foot parts 30 at their bottom; two or more head-foot connecting members 29 connecting the head frame 12 and the foot frame 13; drivers for vertically moving the bed floor (actuators 22 and 23); and rollers 33 with brakes attached to the bottom of the foot parts 30. As shown in FIG. 3(a), the reinforcing members 32 are welded to the head frame 12 and the foot frame 13 of the bed-floor support body. As shown in FIG. 3(b), the suspension members 15 are supported by respective rotary shaft pins 14 and suspended around the top of the reinforcing members 32. Thus, the bed floor is suspended by the bed-floor support body of the bed body in the first embodiment. FIG. 3(a) is a front view of the bed body as seen from outside the foot frame 13, and FIG. 3(b) is a plan view of the foot frame 13 as seen from above.

Figure 4A:
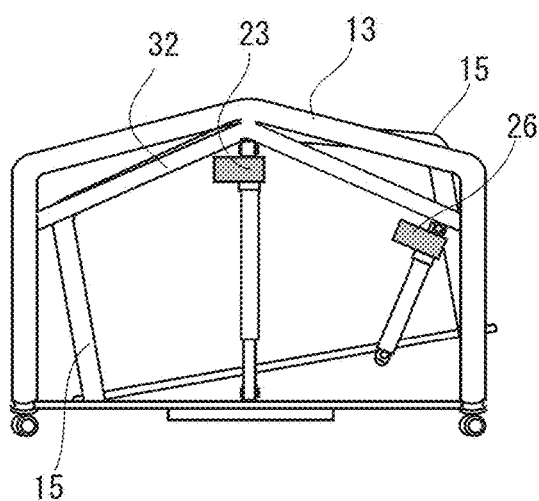
FIGS. 4(a) and 4(b) are front views of the bed body in the first embodiment as seen from the foot frame when a suspension member 15 is tilted in the lateral direction.
Figure 4B:
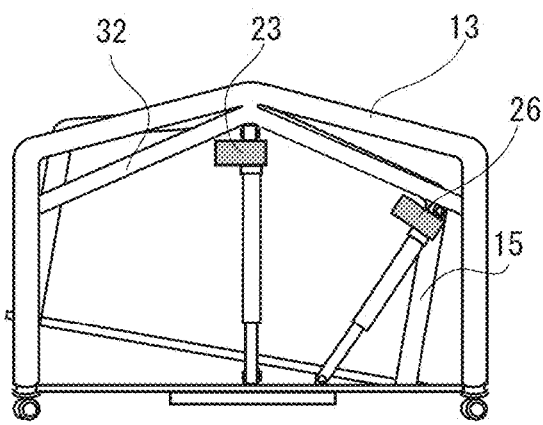

The suspension members 15 each include a driver 26 for tilting the bed floor in the lateral direction, so that the bed floor can be tilted in the lateral direction (can be rotated about the rotary shaft pin 14) (see FIGS. 4(a) and 4(b)). The driver 23 for vertically moving the bed floor (the driver 22 is on the head frame side), the driver 26 for tilting the bed floor in the lateral direction, the driver 19 for the head-receiving surface, the driver 18 for the back-receiving surface, and the knee bending driver 21 are connected to the operating unit 11 via lead wires 31. This allows the operating unit 11 to drive each driver. The driver 26 for tilting the bed floor in the lateral direction is attached to the suspension member 15 on the foot frame 13 side only in FIG. 1, but may alternatively be attached to the member 15 on the head frame 12 side, or to the members 15 on both sides.

Figure 6:
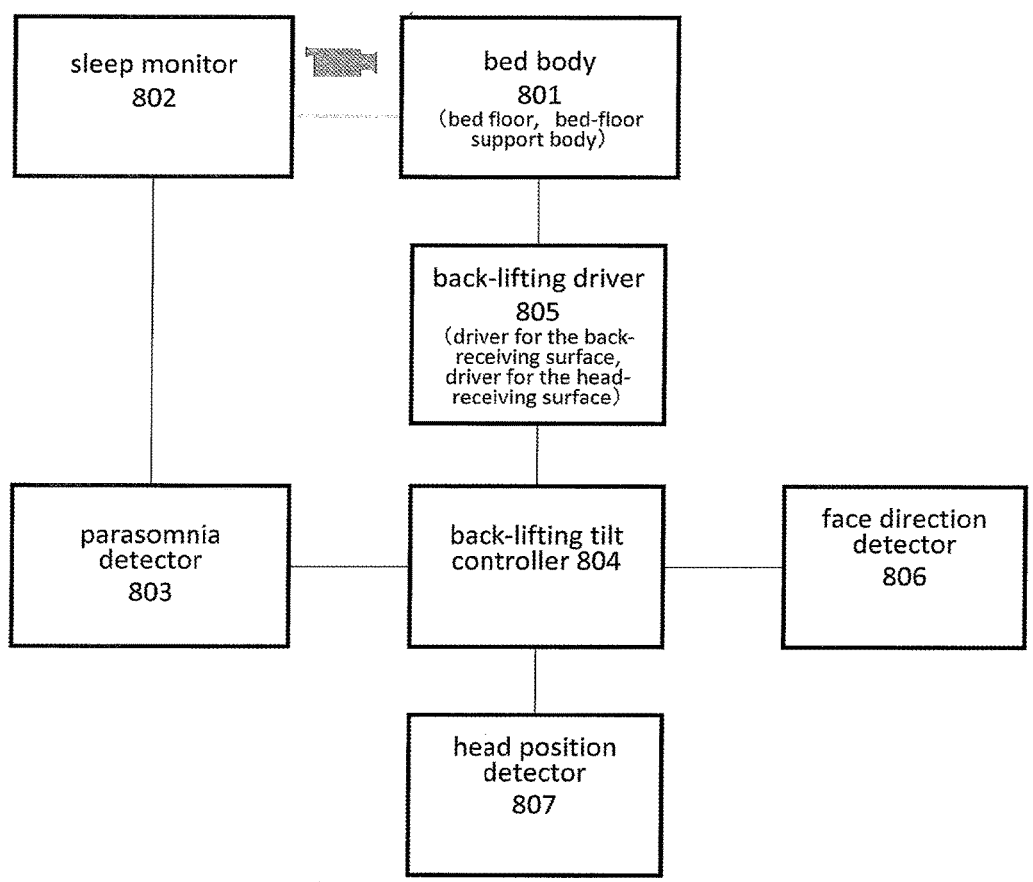
FIG. 6 is a block diagram of the overall structure of the sleeping-posture-control bed system of the first embodiment.

FIG. 6 is a block diagram of the bed system of the present embodiment. The bed system includes a bed body 801 including the bed floor and the bed-floor support body; a sleep monitor 802; a parasomnia detector 803; a back-lifting tilt controller 804; a back-lifting driver 805; a face direction detector 806; and a head position detector 807. The back-lifting driver 805 performs back lifting under the control of the back-lifting tilt controller 804. Of these components, the sleep monitor 802, the parasomnia detector 803, the back-lifting tilt controller 804, the face direction detector 806, and the head position detector 807 are included in the operating unit.

In this configuration, the sleep monitor 802 monitors and detects at least one of the following monitoring elements, which are indicators of parasomnias. Examples of the monitoring elements include heart rate, blood pressure, body temperature, body surface temperature, brain waves, blood oxygen levels, the number of body movements, changes in body posture, the amount of $CO_2$ in the atmosphere around the user, the gas flow rate around the mouth and nose of the user, snoring sound, and teeth-grinding sound. In order to detect these monitoring elements, the sleep monitor includes, near the bed body, at least one of the following devices: an overnight polysomnography; a brain wave sensor; a biosensor for measuring and recording electrocardiogram/heartbeat/body surface temperature/triaxial acceleration (posture) in real time; a pulse oximeter for monitoring pulse rate and saturation of pulse oximetry oxygen ($SpO_2$); a sheet-like multipoint pressure sensor for monitoring body movements; a radio frequency sensor for body movements; a monitoring camera; an air-flow sensor; a gas component sensor; a sound sensor; and a vibration sensor.

The parasomnia detector 803 determines the presence or absence of parasomnias on the basis of the monitoring data of the sleep monitor 802. The parasomnia detector 803 may be configured to determine the presence or absence of parasomnias by comparing the information detected by the sleep monitor 802 with criteria information stored in the storage device and then to determine the type of parasomnias.

The head position detector 807 detects the presence or absence and position of the user's head on the head-receiving surface. This detection is performed by comparing the information of the head detector attached to the head-receiving surface with the information stored in the storage device. The face direction detector 806 determines the face direction of the user. One approach to detecting the head position and the face direction is to use a monitoring camera as a main element of the head position detector 807 or the face direction detector 806, and to compare information taken with the monitoring camera with the information stored in the storage device. Another approach is to compare the pressure distribution information of the pressure-sensitive sheet 36 (see FIG. 5) laid on the head-receiving surface portion 17 with the information stored in the storage device.

The back-lifting tilt controller 804 determines the tilt angle of each of the back- and head-receiving surfaces on the basis of the monitoring data of the sleep monitor 802 and the detection information of the head position detector 807 and the face direction detector 806. The back-lifting tilt controller 804 then tilts the back- and head-receiving surfaces as determined. The tilt angle θx of the back-receiving surface and the tilt angle θy of the head-receiving surface at some time point may be stored in the memory of the back-lifting tilt controller 804. Alternatively, the tilt angle of the back-receiving surface and/or the tilt angle of the head-receiving surface may be divided into multiple steps, and the tilt step number of each of the back- and head-receiving surfaces may be stored in a counter formed in the back-lifting tilt controller 804.

FIG. 5 omits a mattress and a mattress pad, which are generally placed on the bed, and a pillow, which is generally placed under the user's head. If the mattress pad or the like present between the bottom surface and the user disturbs the function of the pressure-sensitive sheet to detect the movements of the user's body and head, the pressure-sensitive sheet is placed on either the mattress pad or the pillow. In this situation, it is possible to adjust the tilt step number of each of the back- and head-receiving surfaces depending on the thickness of the mattress pad or the pillow. Alternatively, it is possible to provide a monitoring camera at a side of the bed in order to detect the bending of the neck and head from an image. In either case, the tilt angles of the back- and head-receiving surfaces can be adjusted to be equivalent to the bending of the neck under the conditions that there is no mattress pad or the like between the user and the bottom surface and that Mathematical Formula (1), (2), or (3) shown below is satisfied.

It is preferable that the mattress and the mattress pad to be placed on the bottom surface be easily bendable, for example, locally bendable (such as a mattress with seams, a mattress made of natural rubber or foamed urethane with nicks at which the mattress is bent). The mattress and the mattress pad are placed on the bed bottom surface so that their bending portions coincide with the bending portions of the bed bottom surface. The mattress pad may be fixed to the bottom surface using a fixing means such as a zipper, buttons or a band. This prevents the mattress pad from slipping down the bed bottom surface while the bottom surface is lifted or tilted in the lateral direction.

If the user's face is not up (supine), or his/her head is not in the central region of the head-receiving surface in the vertical direction, the tilting of the back- and head-receiving surfaces may not have the effect of widening his/her airway. Therefore, the back-lifting tilt controller 804 is preferably configured to operate as follows. The back- and head-receiving surfaces are tilted only when the effect of reducing parasomnias can be anticipated from the information of the parasomnia detector 803, the head position detector 807, and the face direction detector 806. When such a reduction effect cannot be anticipated, instead of tilting the back- and head-receiving surfaces, a warning can be issued to the user or the helper by, for example, sounding a beeper or showing a warning sign on the display screen. It is also preferable to issue such a warning also when the tilt angles of the back- and head-receiving surfaces are at their maximum when abnormality is detected and cannot be tilted any further.

When the user is supine, and his/her head is in the central region of the head-receiving surface in the vertical direction, the back- and head-receiving surfaces are tilted to widen his/her airway. In this situation, the user is monitored to detect apnea or hypopnea. When the user is not supine, if his/her head is not in the central region of the head-receiving surface in the vertical direction or if the parasomnias are not reduced even after the tilt of the head-receiving surface (a negative angle of elevation) is gradually increased up to the maximum, then a beeper is sounded to alert the helper or the user. Note that this is merely one example, and the conditions and procedure of the tilting may be set arbitrarily. As the conditions and procedure of the tilting, software information to drive the back-lifting driver 805 can be stored in the storage device of the back-lifting tilt controller 804.

The back-lifting driver 805, which is a driver for tilting the user's upper body, includes a driver for the back-receiving surface which tilts the back-receiving surface, and a driver for the head-receiving surface which tilts the head-receiving surface. The back-lifting driver 805 controls these drivers so as to bend the back- and head-receiving surfaces into an inverted "V" shape. As a result, the user's body is bent into an inverted "V" shape at his/her neck with his/her head down. As shown FIG. 2, the driver for the back-receiving surface can be composed of the actuator 18, whereas the driver for the head-receiving surface can be composed of the actuator 19.

Similar to the parasomnia detector 803, the storage device only needs to be accessible from the processing unit via a wired or wireless circuit. Furthermore, the processing unit of the parasomnia detector 803 may also serve as the processing unit of the back-lifting tilt controller 804. In addition, the storage device of the parasomnia detector 803 may also serve as the storage device of the back-lifting tilt controller 804.

The operating unit 11 can be composed, for example, of a computer including an arithmetic device, a control device, a storage device, an input device, an output device issuing a warning sound, an ON-OFF switch, and a display device for showing the control state. The arithmetic device and the storage device may be configured to also be used for the parasomnia detector 803, the back-lifting tilt controller 804, the face direction detector 806, and the head position detector 807. Alternatively, each of these components may have an arithmetic device and a storage device of its own. It is possible that some of these components may be connected to each other via wired or wireless communication so that not all components are installed in the operating unit 11. It is also possible that the storage device stores sleep monitoring information, and the doctor acquires the information via communication lines or from external memory so as to examine the user suffering from parasomnias using the information.

The back-lifting driver 805 is composed of the actuator in the first embodiment; alternatively, however, any driving system that can achieve every required movement can be used instead. Each of the inverted U-shaped frames 12 and 13 can include a body formed of a large-diameter pipe and the two foot parts each formed of small-diameter pipes. These different-diameter pipes are slidably combined. In this structure, it is possible to install in the pipes either an actuator or a motor-driven screw or gear mechanism, all of which can move vertically in synchronization with the driver for vertically moving the bed floor (actuator 23).

FIG. 2 shows the bed system when the back-receiving surface portion 16, the head-receiving surface portion 17, the upper-leg-receiving surface portion 24, and the lower-leg-receiving surface portion 25 of the bed floor are lifted. Assume, for example, that the tilt angle θx of the back-receiving surface is 10°; the tilt angle θy of the head-receiving surface with reference to the back-receiving surface is −10° (in this condition, the head-receiving surface is parallel to the surface on which the bed is placed); the angle of the upper-leg-receiving surface is 12°; and the angle of the lower-leg-receiving surface with respect to the upper-leg-receiving surface is −10°.

In this case, the included angle between the back-receiving surface portion 16 and the head-receiving surface portion 17 varies as shown in FIG. 5 from the state shown in FIG. 1 to the state shown in FIG. 2 (in the course of lifting the head-receiving surface portion 17). The relation between the tilt angle θx of the back-receiving surface portion 16 and the tilt angle θy of the head-receiving surface portion 17 with reference to the back-receiving surface portion 16 is controlled to satisfy one of the following mathematical formulas (1) to (3):

$$0°<\theta x \leq 70°, -45° \leq \theta y<0°, \text{ and } -30° \leq \theta x+\theta y \quad (1)$$

$$0°<\theta x \leq 70°, -45° \leq \theta y<0°, \text{ and } 0° \leq \theta x+\theta y \quad (2); \text{ and}$$

$$2° \leq \theta x \leq 85°, -45° \leq \theta y \leq -2°, \text{ and } 0° \leq \theta x+\theta y \quad (3).$$

Note that the tilt angle θy is a negative value when it is smaller than the angle of an extended line of the back-receiving surface.

The angle of the back-receiving surface portion 16 and the magnitude of the tilt angle of the head-receiving surface portion 17 with reference to the back-receiving surface portion 16 needs to be set appropriately depending on the clinical condition of the user because it greatly affects his/her parasomnia. For example, a patient with severe sleep apnea syndrome needs to have his/her head tilted far back (bent in the negative direction) to establish an open airway. The bed system 1 of the present invention is configured to increase the |θy| (to tilt the head back) with an increase in the tilt angle θx, not to tilt only the user's head far back in the negative direction (to increase |θy|). This configuration prevents the user's head from being lower than the horizontal surface (the surface on which the bed is placed), thereby preventing too much blood from rushing to his/her head.

If, however, the |θy| is very large, the user is subjected to a large load, and may have a neck sprain. To avoid this, the angles θx and θy are set appropriately depending on the user's age, health status, and clinical condition. More specifically, [θx+θy] can be not less than 0°, and preferably be one of the following: larger than 0°, not less than 2°, not less than 5°, not less than 7°, and not less than 10°. The lower limit of the tilt angle θy is set to −45°, and more preferably be one of the following: 30°, 20°, 10°, 5°, and 3°. When the bed system 1 is applied to bedridden elderly people, it is preferable that −20°<θy<−3°.

The head-receiving surface is constantly set to not less than 0° ([θx+θy] is not less than 0°) with respect to the bottom surface (the surface perpendicular to the direction of gravity), and the back-receiving surface is tilted to form an inverted "V" shape with the head-receiving surface. This configuration keeps the user's head higher than his/her heart, preventing too much blood from rushing to his/her head. As a result, the user's airway can be widened without a large load being applied to the user.

In the sleeping-posture-control bed system of the first embodiment, the back- and head-receiving surface portions 16 and 17 are driven separately by the two drivers (the driver 18 for the back-receiving surface and the driver 19 for the head-receiving surface, respectively). These drivers are configured to be driven under the tilt conditions set by the operating unit 11, but this configuration does not limit the present invention thereto. For example, it is alternatively possible to form a quadric crank mechanism including the back- and head-receiving surface portions 16 and 17: the back-receiving surface portion 16 is lifted by an actuator, and the head-receiving surface portion 17 is lifted in conjunction with this. A similar structure can be applied to the upper-leg-receiving surface portion 24 and the lower-leg-receiving surface portion 25. Furthermore, at least one component of the quadric crank mechanism can be made variable to adjust the tilt of the head-receiving surface portion 17. It is also possible to provide a driver (for example, an actuator) to the head-receiving surface portion so as to control the tilt of the head-receiving surface.

Figure 24:
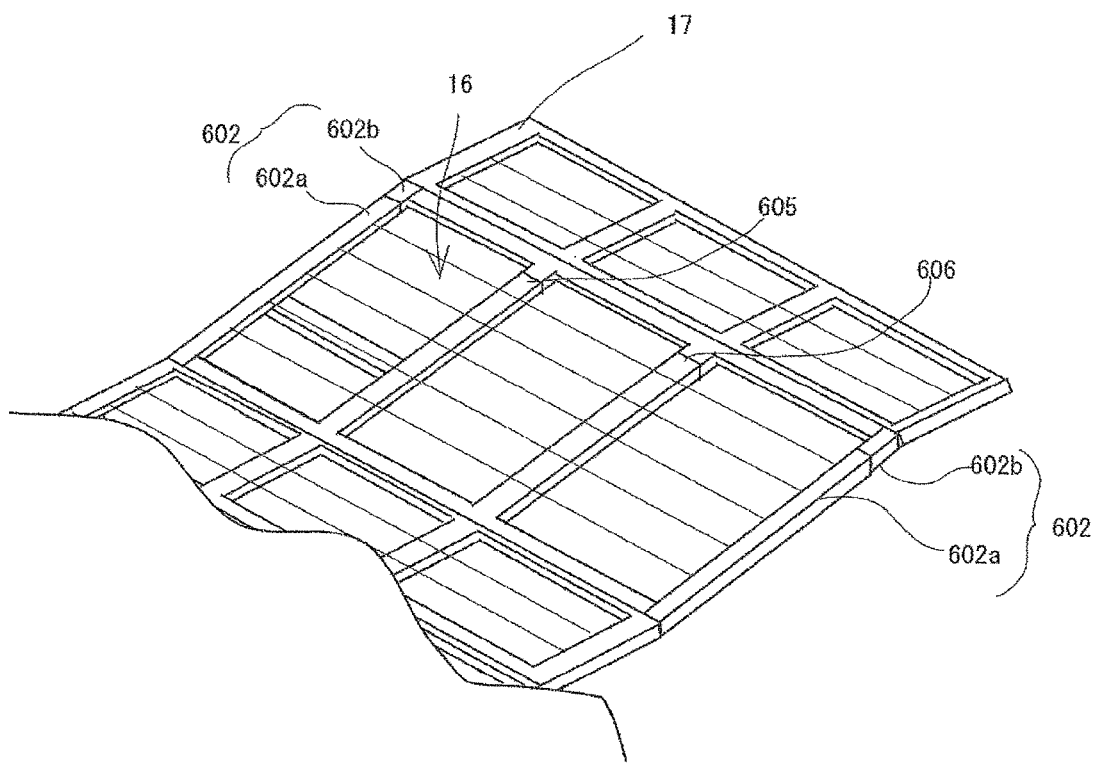
FIG. 24 is a perspective view of a longitudinally stretchable back-receiving surface portion as a modified example of the back-receiving surface portion used in the first embodiment.

In the bed floor of the bed system of the first embodiment, it is preferable that the back-receiving surface portion 16 be configured to be stretchable in the longitudinal direction of the bed depending on the length of the user's body so that the user's head can be on the head-receiving surface portion 17 when the back-receiving surface portion 16 is lifted on the head-receiving surface portion 17 side. Such a modified example will now be described with reference to FIG. 24 and FIGS. 25(1) to 25(3). FIG. 24 shows an example in which the longitudinal length of the back-receiving surface portion 16 is minimized.

Figure 25:
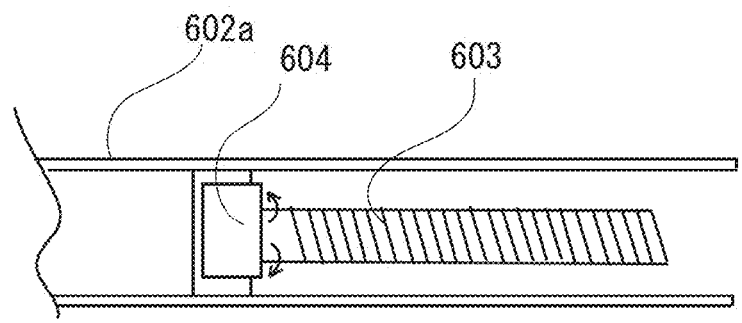
FIGS. 25(1)-25(3) are explanatory drawings of members for stretching the back-receiving surface.
Figure 25:
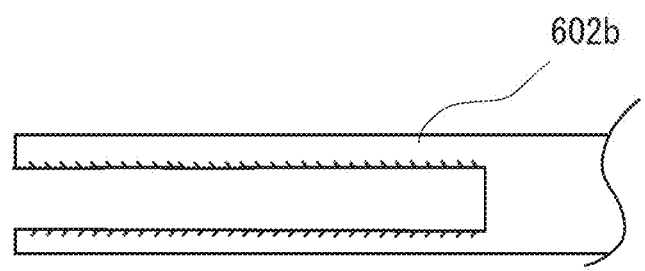
Figure 25:
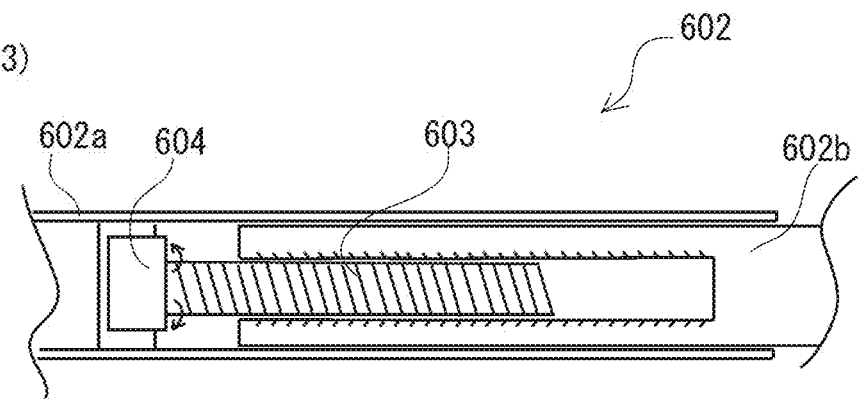

As shown in FIGS. 25(1) to 25(3), a back-receiving-surface longitudinal frame 602 is composed of a back-receiving-surface longitudinal main member 602a and a back-receiving-surface longitudinal elastic member 602b, which slides inside the member 602a. The member 602a includes a rotary rod 603 in its inside space and a motor 604 for driving the rod at the back of the space. The rotary rod has a spiral groove on its outer periphery, and the tip of the rotary rod faces the opening. The motor 604 is configured to rotate the rotary rod forward or backward, and is connected to the operating unit 11 so as to be controlled by it.

Meanwhile, the back-receiving-surface longitudinal elastic member 602b has a hollow inside, and the inner wall of the hollow is provided with a groove meshing with the spiral groove of the rotary rod 603. The elastic member 602b is inserted in the main member 602a in such a manner that the groove meshes with the spiral groove of the rotary rod 603, thereby forming the back-receiving surface portion 16. FIG. 25(3) shows the main member 602a and the elastic member 602b inserted therein.

The longitudinal length of the back-receiving surface portion 16 with this configuration can be adjusted depending on the length of the user's body by rotating the motor 604 forward and backward so that the user's head can be placed on the head-receiving surface portion 17. This adjustment can be achieved as follows. For example, the helper can operate the operating unit 11 while checking the lifted angle and position of the user's head. Alternatively, the computer of the operating unit 11 can be configured to automatically control the direction and amount of rotation of the motor 604 on the basis of the information from the head position detector (see FIG. 6), which will be described later.

It is also preferable that longitudinal reinforcing members 605 and 606 shown in FIG. 24 are configured to be stretchable with the back-receiving surface portion 16 by the following manner. The members on the back-receiving-surface longitudinal elastic member side are made smaller in diameter than the members on the back-receiving-surface longitudinal main member side, so that these members can be slidably engaged with each other. However, these members 605 and 606 do not need to have a stretching mechanism including the rotary rod with the spiral groove and the motor. Instead of configuring the members 605 and 606 to follow the stretching of the back-receiving surface portion 16, a gap may be formed between the members on the back-receiving-surface longitudinal elastic member side and the members on the back-receiving-surface longitudinal main member side when the portion 16 is stretched. In the case that the head-receiving surface portion 17 is driven by a driving force (for example, an actuator) different from the one used for the portion 16, the driving force is adjusted to follow the stretching of the portion 16. For example, the arm length of the actuator can be configured to be automatically adjusted.

The above-described stretching mechanism includes the motor-driven rotary rod with the spiral groove, but other stretching mechanisms can be employed. For example, the back-receiving surface portion 16 can have an accordion-folded structure stretchable in the longitudinal direction. The stretching of the accordion-folded structure is adjusted by pulling this structure from one side by a spring mechanism and from the other side by a power mechanism.

To make the structure more understandable, FIG. 5 shows the user lying directly on the bed bottom surface, but usually, a mattress pad and a mattress are placed on the bed bottom surface and also a pillow under the user's head. It is preferable that the mattress pad and the mattress to be placed on the bed bottom surface have a fold line at the boundary between the back- and head-receiving surfaces so as to be easily bent into an inverted "V" shape. In the case of using a common mattress pad or mattress with a uniform thickness and not using a pillow, the crossing angle between the back- and head-receiving surfaces can be actually calculated by using the angles of the back- and head-receiving surfaces. If, however, compression of the mattress pad due to the user's weight is not negligible, it is preferable to correct the angle.

When a pillow is placed under the user's head in addition to the mattress pad and the like, at least the thickness of the pillow affects the angle of the neck. Therefore, the angles in Mathematical Formulas (1) to (3) are adjusted in consideration of the thicknesses of the mattress pad and the pillow so that the crossing angle between the back- and head-receiving surfaces can substantially satisfy one of Mathematical Formulas (1) to (3). More specifically, in the case of using a mattress pad, a mattress, and a pillow, it is preferable to adjust the tilt angle of the head-receiving surface (the angles in Mathematical Formulas (1) to (3) shown above) depending on the thickness of each of the mattress pad, the mattress, and the pillow. This allows the tilt of the head with respect to the body center line 35 (see FIG. 5) (bending of the neck) to be equivalent to the angles in Mathematical Formulas (1) to (3).

The following is a description, with reference to FIG. 5, of the relation between the user's sleeping posture and the movements of the back- and head-receiving surface portions 16, 17 and the upper-leg-receiving surface portion 24 and the lower-leg-receiving surface portion 25. The surface of the bed floor on which the user lies (the arrow "a" in FIG. 5) is generally horizontal (the surface perpendicular to the vertical axis). When a component of the operating unit 11 detects the user's parasomnia, the driver 18 for the back-receiving surface and the driver 19 for the head-receiving surface lift the back- and head-receiving surface portions 16 and 17, respectively (the arrows "b" and "c" in FIG. 5) of the bed floor. This lifting is performed in accordance with the instructions from the operating unit in such a manner as to satisfy Mathematical Formula (1), (2) or (3). This lowers the user's head, thrusts out his/her chin, and widens his/her airway. If the face direction detector 806 and the head position detector 807 detect that the user's face is not up (supine) or his/her head is not in the central region of the head-receiving surface portion 17 in the vertical direction, a warning sound can be issued without moving the back-receiving surface portion 16 or the head-receiving surface portion 17 vertically.

$$0°<\theta x \le 70°, -45° \le \theta y<0°, \text{ and } -30° \le \theta x+\theta y \quad \text{Mathematical Formula (1)}$$

$$0°<\theta x \le 70°, -45° \le \theta y<0°, \text{ and } 0° \le \theta x+\theta y \quad \text{Mathematical Formula (2)}$$

$$2° \le \theta x \le 85°, -45° \le \theta y \le -2°, \text{ and } 0° \le \theta x+\theta y \quad \text{Mathematical Formula (3)}$$

Figure 7:
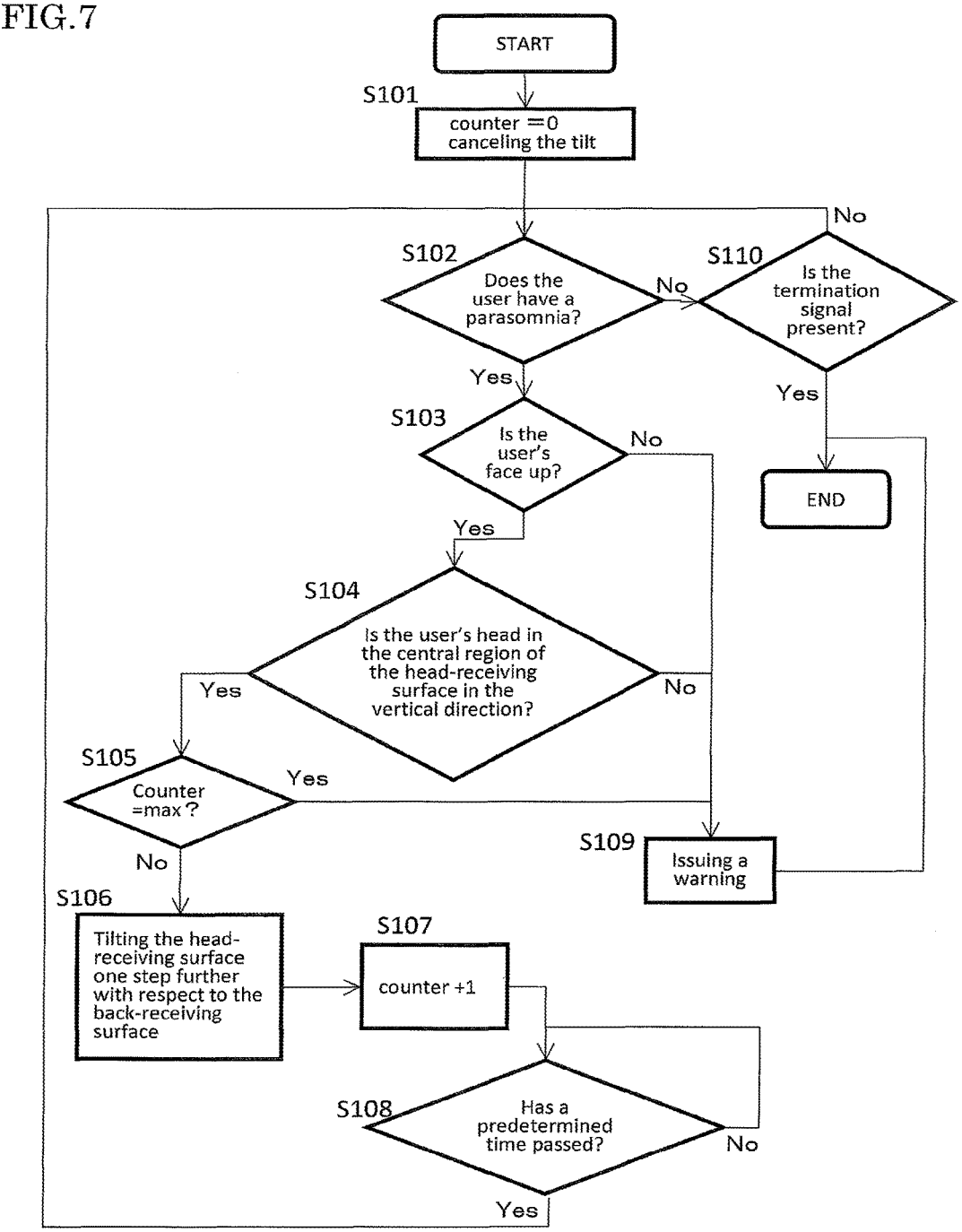
FIG. 7 is a flowchart showing the operation of the sleeping-posture-control bed system of the first embodiment.

The flowchart showing the basic operation of the sleeping-posture-control bed system of the first embodiment will now be described in the case of monitoring the user's sleep apnea syndrome as a parasomnia with reference to FIG. 7.

The process is started when the power switch is turned on and the presence of the user on the bed floor is detected.

Step S101

This process is started from the state in which neither the back-receiving surface nor the head-receiving surface is tilted. First, a switch in the operating unit is operated to cancel the tilt (the bottom surface is made horizontal), and the counter to store the tilt step number is reset to 0.

Step S102

Next, the parasomnia detector determines the presence or absence of parasomnias from the monitoring information of the sleep monitor. If the user is determined to have parasomnia, the process proceeds to Step S103; otherwise to Step S110.

Step S103

The face direction detector determines the user's face direction from the information of the head position detector. When the face is up, the process proceeds to Step S104; otherwise to Step S109.

Step S104

The head position detector detects the head position on the head-receiving surface. When the head is in the central region in the vertical direction, the process proceeds to Step S105; otherwise to Step S109.

Step S105

The tilt step of each of the head- and back-receiving surfaces at the present moment is determined from the above-mentioned counter information. If the tilt step number is not at maximum, the process proceeds to Step S106; otherwise to Step S109.

Step S106

Since the head- and back-receiving surfaces can be tilted further, they are tilted one step farther so as to widen the user's airway. Then, the process proceeds to Step S107. The storage device of the back-lifting tilt controller 804 stores the tilt angle $\theta x$ of the back-receiving surface; the tilt angle $\theta y$ of the head-receiving surface, and their sum $\theta x+\theta y$ (satisfying at least one of mathematical formulas (1) to (3)) by dividing them in multiple steps. The back-lifting tilt controller 804 controls the operation of the back-lifting driver on the basis of this information, thereby tilting the back-receiving surface and/or the head-receiving surface.

Step S107

The counter is incremented by 1 to update the tilt step number stored therein. Then, the process proceeds to Step S108.

Step S108

If this tilting procedure causes sleep monitoring to be resumed before the user recovers from the abnormal condition, the head and back-receiving surfaces may be tilted too much. To avoid this, after the tilting procedure, it is confirmed that a predetermined time has passed before the sleep monitoring is resumed. When it is confirmed, the process returns to Step S102 to continue the sleep monitoring; otherwise, Step S108 is repeated. The predetermined time can be set, for example, to three, five, or ten minutes and be stored by a doctor, a nurse, or the like.

Step S109

In this step, parasomnias are present and also the user is in one of the following conditions: (1) the face is not up; (2) the head is not in the central region of the head-receiving surface in the vertical direction; and (3) the tilt is already at its maximum. These cases indicate that either the user cannot be expected to recover from the parasomnia even if the head- and back-receiving surfaces are tilted, or the headand back-receiving surfaces cannot be tilted any further. Therefore, a warning is issued to indicate that the user has a parasomnia. The warning can be, for example, directly alerted to the user as voice, vibration, etc. or be informed to the helper as warning voice, vibration, warning image, etc.

Step S110

When the parasomnias are absent, it is determined whether the termination signal is present or not. The termination signal is determined to be present when the termination signal switch is turned off or when the user is not detected in bed. When the termination signal is absent, the process proceeds to Step S102 where the presence or absence of the termination signal continues to be detected while the user's parasomnias are continuously monitored. When the termination signal is present, a termination operation is performed. The termination operation may alternatively be performed after the tilt is cancelled.

Modified Flowchart of the First Embodiment

Figure 8:
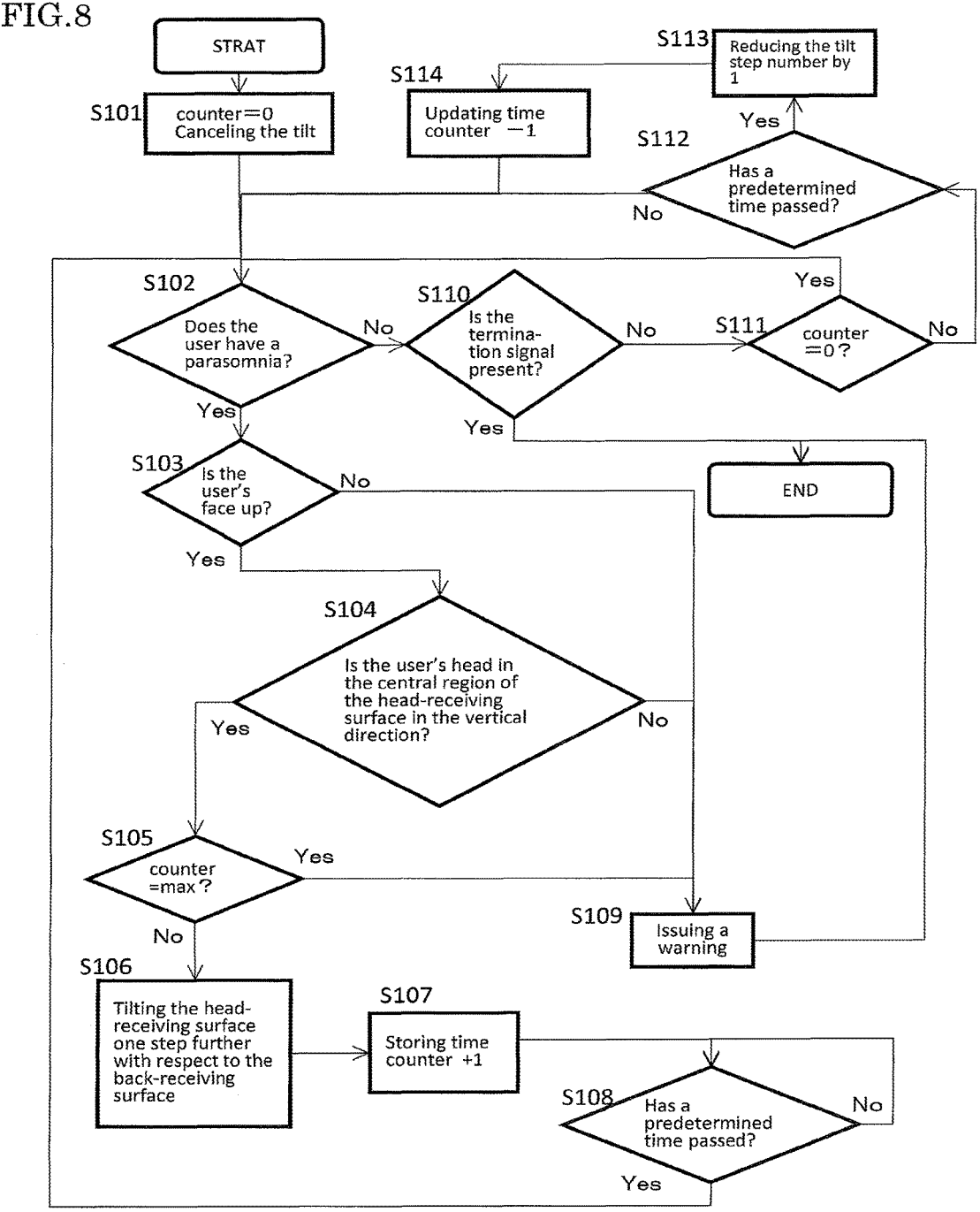
FIG. 8 is a modified flowchart showing the operation of the sleeping-posture-control bed system of the first embodiment.

As shown in FIG. 8, when parasomnias are not detected for the predetermined time, the head- and back-receiving surfaces can be put back to their original horizontal positions. The following description will be focused on difference between the flowchart shown in FIG. 8 and the flowchart shown in FIG. 7.

Step S107

The counter is incremented by 1 to update the tilt step number stored therein. In addition, the time when the tilting procedure is completed is stored in the timer. Then, the process proceeds to Step S108.

Step S110

When the parasomnias are absent, it is determined whether the termination signal is present or not. The termination signal is determined to be present when the termination signal switch is turned off or when the user is not detected in bed. When the termination signal is absent, the process proceeds to Step S111.

Step S111

Before proceeding to the monitoring of parasomnias, it is determined whether the head- and back-receiving surfaces are tilted at the present moment or not. When they are not tilted (the counter storing the tilt step number shows 0), the process returns to Step S102 to keep monitoring the parasomnias; otherwise (the counter shows other than 0) the process proceeds to Step S112.

Step S112

The time the head- and back-receiving surfaces are tilted is confirmed to determine whether a predetermined time has passed since the time the tilting procedure is completed. This predetermined time can be set, for example, to 20 or 30 minutes and be stored by the doctor, the nurse, or the like. When the predetermined time has passed, the process proceeds to Step S113; otherwise to Step S102.

Step S113

The tilt step number of each of the head- and back-receiving surfaces is reduced by 1, and the process proceeds to Step S114.

Step S114

The counter is decremented by 1 to update the tilt step number stored therein. In addition, the time when the tilting procedure is completed is updated in the timer. Then, the process proceeds to Step S102 to resume sleep monitoring.

The tilt is returned one step at a time in the above-described example, but may alternatively be returned by two or more steps at a time, or be reset to 0 after a predetermined time has passed. The cancellation of the tilt and the reset of the counter (in Step S101) may alternatively be performed upon detection of the switch-off operation or the user's absence (after Step S110 and before the end of the process).

In the case that the longitudinal length of the back-receiving surface portion 16 is stretchable, the back-lifting tilt controller 804 can include a memory to store the longitudinal length of the portion 16, and the operational flowchart in FIG. 7 can be modified as follows. First, in Step S101, in addition to resetting the counter and cancelling the tilt, the longitudinal length of the back-receiving surface portion 16 is set to the default state (the length when the back-receiving surface is not tilted), and the memory to store the longitudinal length is reset.

Between Steps S106 and S107 are added additional steps: a step of determining the presence or absence of change in the longitudinal length on the basis of the information from the head position detector 807; and a step of changing (increasing or decreasing) the longitudinal length of the back-receiving surface portion 16 when the change in the longitudinal length is determined to be present. At this moment, the back-lifting tilt controller 804 determines the amount of change in the longitudinal length of the portion 16 on the basis of the software information stored in the storage device, and controls the operation of the back-lifting driver 805 so as to change the longitudinal length of the portion 16.

In Step S107, the counter is incremented by 1, and the longitudinal length of the back-receiving surface is updated.

Figure 9:
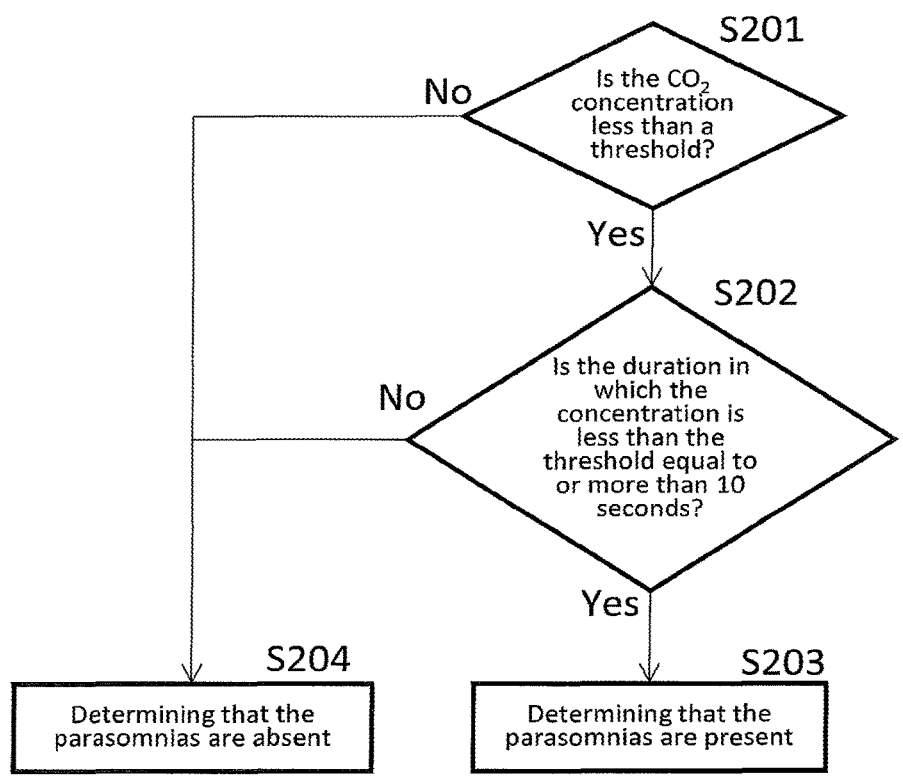
FIG. 9 is a flowchart of the determination of the presence or absence of parasomnias by the sleeping-posture-control bed system of the first embodiment.

The flowchart for determining the presence or absence of parasomnias will be described with reference to FIG. 9. FIG. 9 illustrates a flowchart of the determination of the presence or absence of parasomnias. The following will describe the determination of the presence or absence of sleep apnea by monitoring $CO_2$ concentration information in the user's exhaled breadth.

Step S201

When the operation is started, first of all, the $CO_2$ concentration sensor starts to continuously monitor the gas component concentration around the user's mouth and nose. When the concentration is determined to be less than a threshold (indicating hypopnea or apnea), the process proceeds to Step S202; otherwise (not less than the threshold) to Step S204.

Step S202

When the concentration is determined to be less than the threshold, the detector calculates the time during which the concentration is less than the threshold. When this duration is equal to or more than a predetermined time (for example, ten seconds), the process proceeds to Step S203; otherwise to Step S204.

Step S203

When the concentration less than the threshold continues for the predetermined time or more, the user has hypopnea or apnea. As a result, the parasomnia is determined to be present.

Step S204

When the concentration is not less than the threshold, or the concentration less than the threshold does not continue for the predetermined length or more, the user does not have hypopnea or apnea. As a result, the parasomnia is determined to be absent.

The sleeping-posture-control bed system described above includes only minimum components, but may include other additional components such as frames or reinforcing members to reinforce the bed body or the bed bottom.

The bed system may further include a controller allowing the user or the caregiver to control the tilts by themselves.

As described above, in the present embodiment, the user's airway can be widened by tilting the back- and head-receiving surfaces of the bed floor. This has the effect of reducing or eliminating parasomnias caused by the narrowed airway.

Second Embodiment

Figure 10:
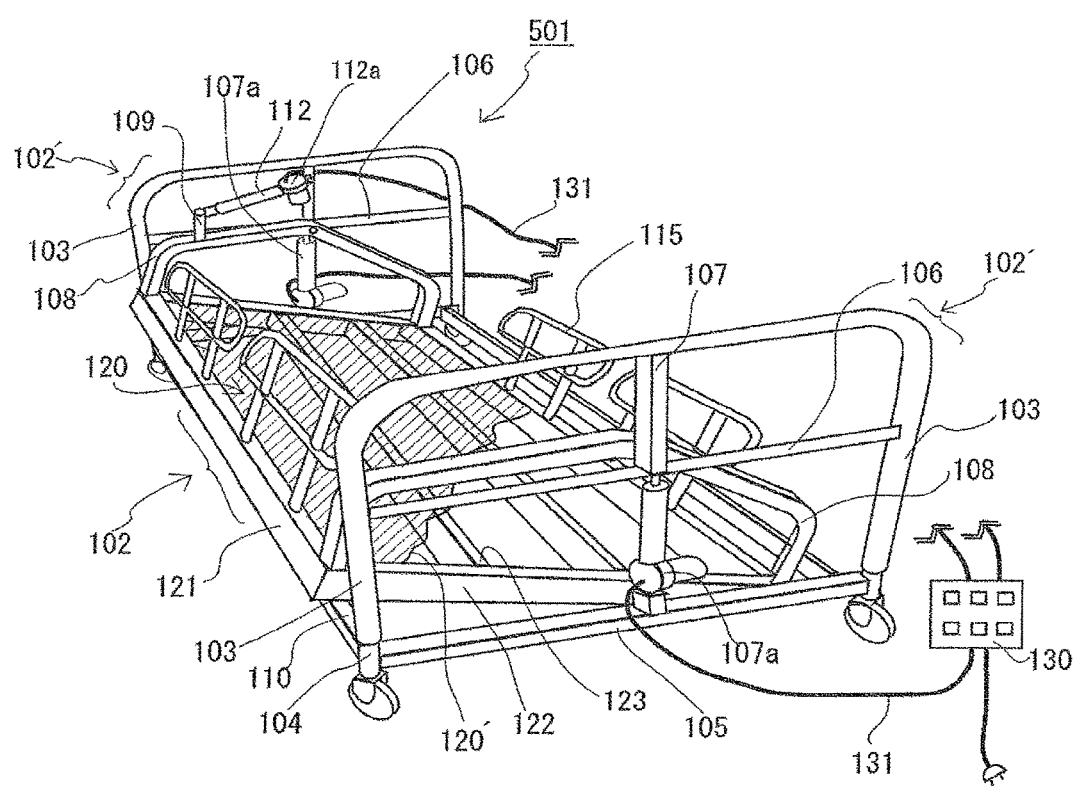
FIG. 10 is a perspective view of a bed body in a second embodiment.
Figure 11:
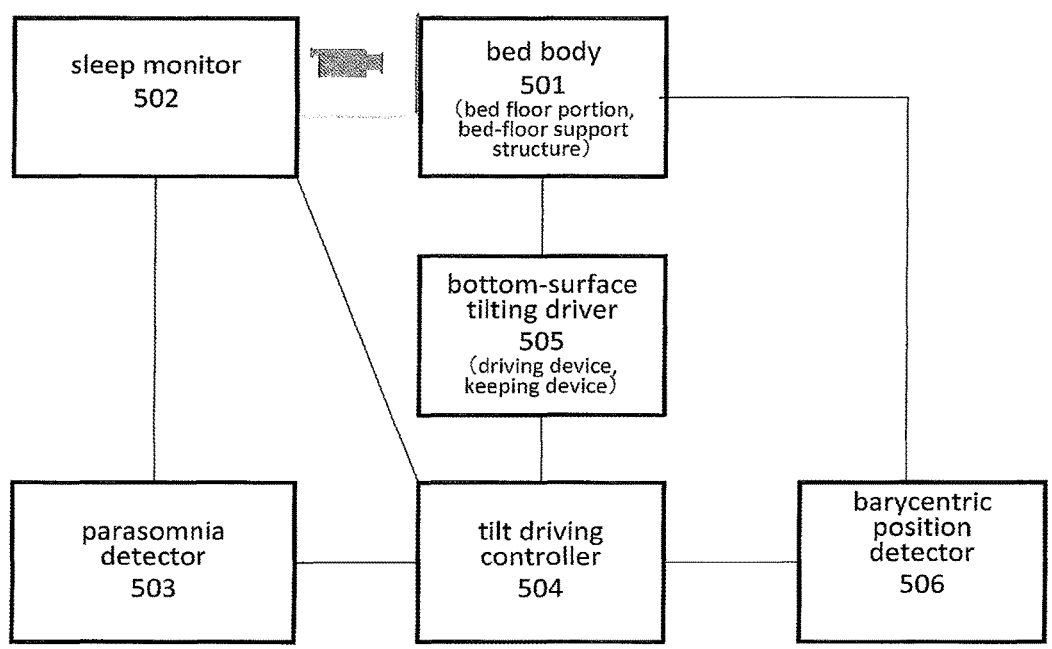
FIG. 11 is a block diagram of the overall structure of the sleeping-posture-control bed system of the second embodiment.

FIG. 10 shows a bed body of a sleeping-posture-control bed system of a second embodiment of the present invention, and FIG. 11 shows its overall structure (block diagram). The bed system of the second embodiment includes a bed body 501 (see FIG. 10) having a suspended bed floor portion 102 with a bottom surface 120; a sleep monitor 502 for monitoring the sleep of the user sleeping on the bottom surface 120; a parasomnia detector 503 for determining the presence or absence of parasomnias from the monitoring data of the sleep monitor 502; a bed-floor tilt driver 505 for tilting the bed floor portion 102 having the bottom surface 120; a tilt driving controller 504 for controlling the bed-floor tilt driver 505 so that the bottom surface 120 can be tilted on the basis of the determination result of the parasomnia detector 503; and a barycentric position detector 506 for detecting the position of the user's center of gravity on the bottom surface (see FIG. 11). In the first embodiment, the head- and back-receiving surfaces are tilted in the direction from the feet to the head. In contrast, in the second embodiment, the entire bottom surface of the bed floor is tilted in the lateral direction.

In the configuration shown in FIG. 11, the sleep monitor 502 monitors and detects at least one of the following monitoring elements, which are indicators of parasomnias, and the face direction of the user lying. Examples of the monitoring elements include heart rate, blood pressure, body temperature, body surface temperature, brain waves, blood oxygen levels, the number of body movements, changes in body posture, the amount of $CO_2$ in the atmosphere around the user, the gas flow rate around the mouth and nose of the user, snoring sound, and teeth-grinding sound. In order to detect these monitoring elements, the sleep monitor includes the followings: a monitoring camera for monitoring the face direction of the user lying, a pressure-sensitive sheet placed on the portion of the bottom surface on which the user's head is positioned, or on a mattress pad or a mattress covering the portion, or on a pillow, or a triaxial sensor attached to the user's head; and at least one of the following sensors for monitoring some monitoring elements, which are indicators of parasomnias, the sensors includidng an overnight polysomnography, a brain wave sensor, a biosensor for measuring and recording electrocardiogram/heartbeat/body surface temperature/triaxial acceleration of the trunk of the body in real time, a pulse oximeter for monitoring pulse rate and saturation of pulse oximetry oxygen ($SpO_2$), a sheet-like multipoint pressure sensor for monitoring body movements, a radio frequency sensor for body movements, a monitoring camera, a an air-flow sensor, a gas component sensor, a sound sensor, and a vibration sensor.

The parasomnia detector 503 determines the presence or absence of parasomnias from the monitoring data of the sleep monitor 502. To achieve this function, the parasomnia detector 503 includes a processing unit such as a central processing unit and a storage device such as a hard disk drive or a flash memory. The detector 503 determines the presence or absence of parasomnias and/or the type of parasomnias by comparing the information detected by the sleep monitor 502 with the criteria information stored in the storage device.

The criteria information is reference information determined by the relationship with the above-mentioned monitoring elements, such as an average person's heart rate, the number of body movements per unit time, body surface temperature, and blood oxygen levels. The types of the parasomnias include apnea, hypopnea, snoring, teeth grinding, abnormal body movement (too many or too few), abnormal body temperature (too low or too high), abnormal blood pressure (too high or too low), and abnormal heart rate (too high or too low).

The storage device only needs to be accessible from the processing unit via a wired or wireless circuit and does not need to be present near the bed. Meanwhile, the processing unit only needs to be configured to acquire monitoring information of the sleep monitor and to perform a determination process, and does not need to be present near the bed.

The tilt driving controller 504 determines the user's face direction from the monitoring information of the sleep monitor 502, and controls the bed-floor tilt driver on the basis of this determination information and the determination result of the parasomnia detector 503 so that the bottom surface can be tilted. To achieve these functions, the controller 504 includes a processing unit such as a central processing unit, and a storage device for storing the information to determine the user's face direction and software information with which to control the bed-floor tilt driver. The tilt driving controller determines the face direction by comparing the information to determine the face direction stored in the storage device of the tilt driving controller with the monitoring information of the sleep monitor. The software information is software information for which the bed needs to be tilted in a direction to allow the bed-floor tilt driver to reduce apnea (to induce the user to a lateral sleeping posture) when the determination result of the parasomnia detector is apnea.

If the user lying supine is detected to have apnea or hypopnea, the bed floor (i.e., the bottom surface) is tilted to induce the user to a lateral (right or left) posture. In this case, the tilt angle is set, for example to 7 degrees. In contrast, if the user lying laterally is detected to have apnea or hypopnea, the user is induced to be supine and then monitored to detect the apnea or hypopnea. If the apnea or hypopnea is not reduced in this condition, the user is induced to the opposite lateral side. If the apnea or hypopnea is not yet reduced (the apnea or hypopnea is detected), the user can be woken up by, for example, a beeper. This tilting procedure can be made arbitrarily, and can be achieved by making the storage device of the tilt driving controller store software information to drive the bed-floor tilt driver. In the same manner, an appropriate procedure can be made also for teeth grinding or snoring, and software information for tilting can be stored in the storage device of the tilt driving controller.

Similar to the above-mentioned parasomnia detector, the storage device only needs to be accessible from the processing unit via a wired or wireless circuit. Furthermore, the processing unit of the parasomnia detector may also serve as the processing unit of the tilt driving controller. In addition, the storage device of the parasomnia detector may also serve as the storage device of the tilt driving controller.

The bed-floor tilt driver 505 tilts the bottom surface of the bed body 501 and keeps the tilt of the bottom surface. The driver 505 may be configured to perform the driving and keeping integrally. Alternatively, it is possible to provide both a driving device for tilting the bottom surface and a keeping device for keeping the tilt of the bottom surface.

The tilt driving controller 504 controls the tilting and keeping of the bed-floor tilt driver 505 integrally. More specifically, the controller 504 controls the operation of the driver 505 so that the bottom surface can be tilted when the parasomnia detector 503 determines the presence of parasomnias. The tilt driving controller 504 can be composed of a well-known control device such as a central control unit (CPU). Alternatively, the control device of the parasomnia detector 503 may also serve as the control device of the tilt driving controller 504.

The barycentric position detector 506 detects the user's center of gravity. The center of gravity is the fulcrum by which the user's full weight can be supported. The detector 506 is configured to detect the position of the projection point when the fulcrum is projected onto the bottom surface. The detector 506 can be composed of a gravity sensor or a multipoint pressure sensor which can be attached to the bed body or to the bed mat to be placed on the bed body. The detector 506 calculates the projection point on the basis of the pressure distribution information of the gravity sensor or the multipoint pressure sensor. The detector 506 may include an image capture device above the bed so that the projection point, which is the center of gravity projected onto the bottom surface, can be calculated through image analysis.

The position information detected by the barycentric position detector 506 is used as follows related to the tilt driving controller 504 and the bed-floor tilt driver 505. Assume that the position of the projection point corresponding to the user's center of gravity (the position detected by the detector 506) at the time when the parasomnia detector 503 determines the presence of parasomnias is lower than the center line of the tilted bottom surface in the tilt direction, the center line being perpendicular to the tilt direction of the bottom surface 120 and including the center point of the area of the bottom surface 120. In this case, the tilt driving controller 504 makes the bed-floor tilt driver 505 tilt the bottom surface 120 so that the position of the projection point corresponding to the user's center of gravity is higher than the center line of the tilted bottom surface, the center line being perpendicular to the tilt direction of the bottom surface 120 and including the center point of the area of the bottom surface 120 (see FIGS. 10 and 11).

Assume that the position of the projection point of the center of gravity moves over the threshold after the bottom surface is tilted with reference to the position of the projection point corresponding to the user's center of gravity on the bottom surface at the time when the presence of parasomnias is determined. Upon receiving this information, the tilt driving controller 504 makes the bed-floor tilt driver 505 decrease the tilt of the bed bottom surface 120. This operation prevents the user from falling off the bed due to a change in his/her posture.

The above-mentioned threshold is determined in consideration of the user's physical strength and clinical condition, the size of the bed bottom area, characteristics of the mat (smoothness of texture, compression-rebound characteristics, compression ratio) etc. The tilt angle of the bottom surface 120 created by the bed-floor tilt driver 505 only needs to be greater than 0 degrees and be not more than 30 degrees or so, and usually in the range of 0 to about 7 degrees. The software information required for the tilting can be stored in the storage device of the tilt driving controller 504.

The following is a description of the components of the bed body 501 shown in FIG. 10. The bed body 501 includes the bed floor portion 102 and a bed-floor support structure 102', which is a support to suspend the bed floor portion 102. The structure 102' includes a driving means for tilting the bed floor portion 102 or driving it up and down. The bed floor portion 102 includes a suspension member 108 for suspending the bed floor portion 102 to the bed-floor support structure 102'; longitudinal bottom-surface frame members 121, lateral bottom-surface frame members 122, and bottom support members 123 which compose the bottom surface 120; and a bottom board 120' placed on the bottom support member 123. The bed surface on or over which the user lies is referred to as the "bottom surface", and in this configuration example, the bottom surface 120 is on the bottom board 120'.

In the bed-floor support structure 102', the bed floor portion 102 is supported and suspended at two positions from outside. The bed-floor support structure 102' includes a tilt control member 112 having a tilt driving means 112a to tilt the bed floor portion 102; a vertically movable frame 107; a vertically driving means 107a for driving the vertically movable frame 107 up and down; two stand frames 103 each having two foot parts 104 stretchable toward the floor surface; a foot-foot connecting frame 105 for connecting the foot parts of the stand frames; a head-foot connecting member 110; a stand connecting frame 106 for fixedly connecting the middle portion of the inverted U-shaped stand frames at an above position; the vertically driving means 107a for connecting the approximate center of the foot-foot connecting frame 105 with the approximate center of the stand connecting frame 106 and for driving also the stand connecting frame 106 up and down; and handrails 115.

The tilt driving means 112a, which composes the bed-floor tilt driver 505 shown in FIG. 11, tilts the bed floor portion 102 (the bottom surface 120) under the control of the tilt control member 112. The vertically driving means 107a drives the bed floor portion 102 up and down. The tilt driving means 112a and the vertically driving means 107a only need to be a mechanism capable of tilting or vertically driving, and have no particular restrictions. For example, they can be configured either to drive and keep the tilt by hydraulic control (integral configuration) or to have a motor for driving the bottom surface and a locking member for locking and keeping the bottom surface tilted (separate configuration). In the configuration example shown in FIG. 10, the tilt driving means 112a is composed of a gear and an electric motor, and the vertically driving means 107a is composed of a hydraulic cylinder and an electric pump.

In the configuration example shown of FIG. 10, the tilt driving means 112a and the vertically driving means 107a are connected to an operating unit 130 via lead wires 131. The operating unit 130 includes the tilt driving controller 504, the parasomnia detector 503, and the barycentric position detector 506 shown in FIG. 11, and also includes an input device (for example, a keyboard) through which the operator enters conditions to control the bed. However, this is only one example, and the operating unit 130 does not necessarily have to include all of the tilt driving controller 504, the parasomnia detector 503, and the barycentric position detector 506. For example, the controller 504 may be integrated with the driver 505.

The configuration of the bed body 501 will now be described in detail with reference to the partially enlarged view of FIG. 12. The two stand frames 103 each include a U-shaped large-diameter pipe and a cylindrical small-diameter pipe which are slidably inserted into each other. The large-diameter pipe has a diameter of 45 mm, an outside width of 1200 mm, and a linear section length of 1100 mm. The small-diameter pipe has a diameter of 42 mm and a length of 900 mm. The foot parts (the sections of the small-diameter pipe extending from the large-diameter pipe) are configured so that their length can be stretched within the range of 100 to 550 mm.

The material of these pipes is not particularly limited and can be, for example, iron, aluminum, titanium, various alloys, or plastic. Their diameters and sizes can be arbitrarily determined. It is also possible to use two separate stand frames that are not U-shaped.

The foot parts of each of the two stand frames are fixedly connected with each other using, as the foot-foot connecting frame 105, a square metal bar (a cross section of 42 mm×42 mm, a length of 1110 mm). The fixed connection can be achieved by welding the square metal bar to the foot parts, connecting them using a connecting fixture, being directly screwed into each other, or any other method.

The stand connecting frame 106 is fixed using a metal bar with a diameter of 45 mm and a length of 1110 mm as the stand connecting frame at a height of 800 mm when the foot parts of the stand frames are minimized in length in the same manner as the foot-foot connecting frame 105.

The vertically movable frame 107 includes a hydraulic cylinder 107*a* as a vertically driving means fixed near the longitudinal center of the foot-foot connecting frame 105. The hydraulic cylinder is attached at its upper end with a metal pipe with a diameter of 45 mm. The tip of the metal pipe is fixed near the center of the stand connecting frame 106. In the example of FIG. 10, a similar metal pipe is fixed between the center of the stand connecting frame 106 and the top of the inverted U shaped. The fixed connection can be achieved by any method; welding or connecting using a connecting fixture can be employed as described above. In this example, the stand frames can be stretched up to 500 mm.

The state of connection between the stand frames 103 and the suspension member 108, and the relationship between the bed body 501, the bottom surface 120, and the suspension member 108 will now be described with reference to FIGS. 12 and 13. FIG. 12 is a partially enlarged view showing the state of connection between the bed floor portion 102 and the bed-floor support structure 102'. FIG. 13(*a*) is a top view of the bed bottom surface 120 covered with a plurality of columnar mat units 125. FIG. 13(*b*) is a cross sectional view taken along arrows A-A of FIG. 13(*a*).

Figure 12:
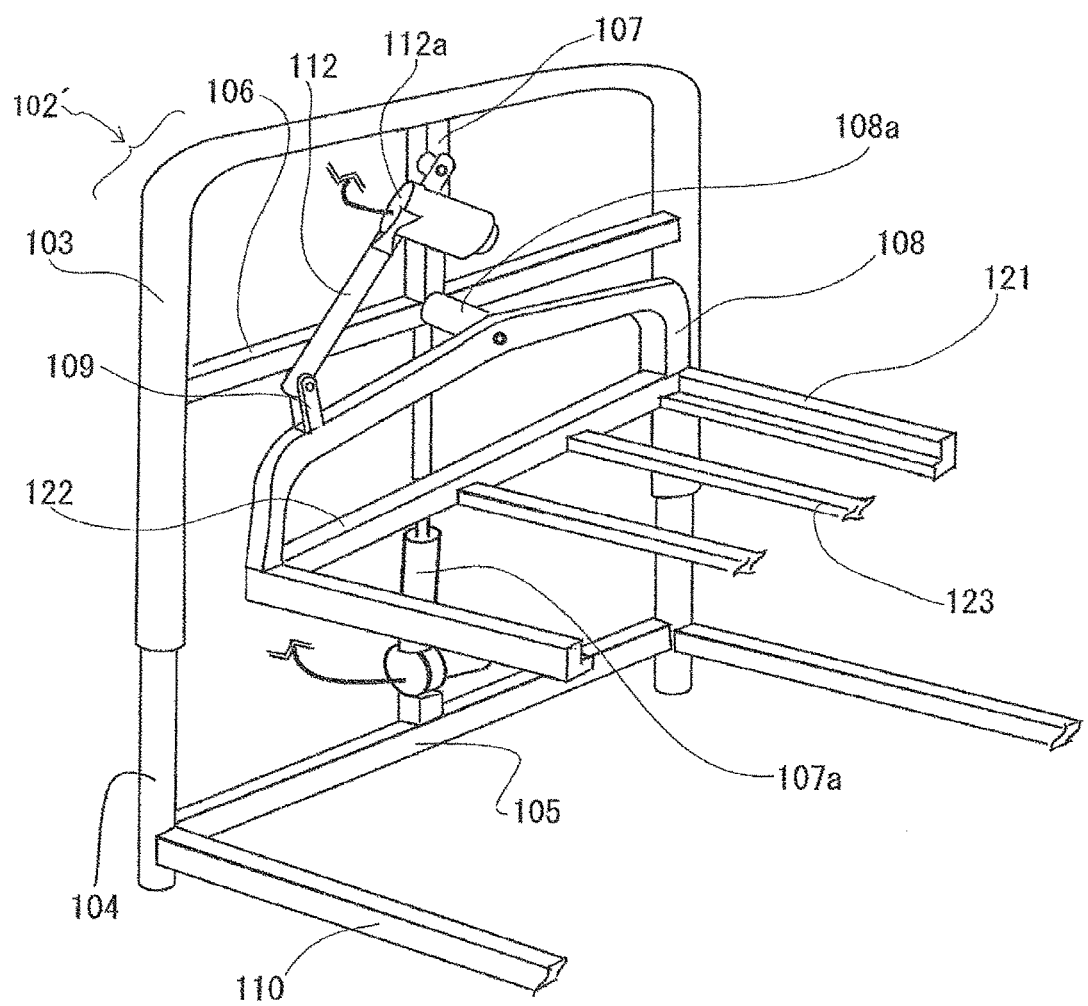
FIG. 12 is a partially enlarged perspective view of the sleeping-posture-control bed system of the second embodiment.
Figure 13A:
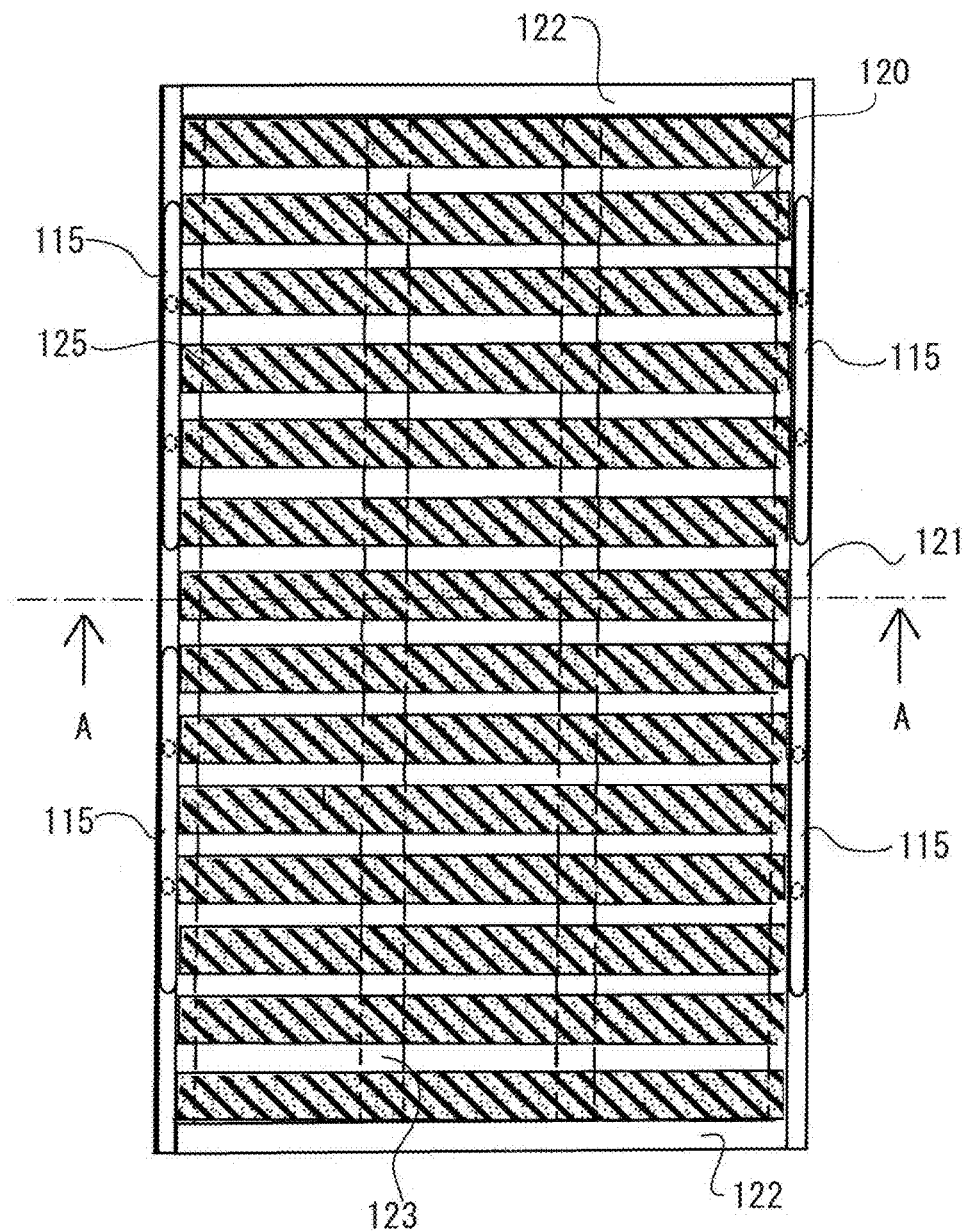
FIG. 13(a) is a plan conceptual view showing columnar mat units laid on the bottom surface of the bed body in the second embodiment.
Figure 13B:
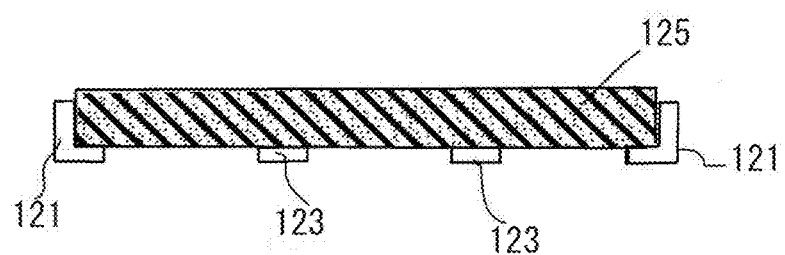
FIG. 13(b) is a sectional view taken along arrows A-A of FIG. 13(a).

As shown in FIG. 12, the suspension member 108 is configured to rotate in the direction perpendicular to the longitudinal direction of the bed (the width direction) described below. The suspension member 108 includes a suspension connector 108*a* forming a suspension shaft. One end of the suspension connector 108*a* is fixed at the intersection between the vertically movable frame 107 and the stand connecting frame 106. The other end is inserted to a rolling bearing with balls, which is formed at the top of the suspension member. The rolling bearing may alternatively be formed at the intersection between the vertically movable frame 107 and the stand connecting frame 106. It goes without saying that the suspension member can be configured to be rotatable by other known method than using the rolling bearing.

In the example of FIG. 12, the longitudinal bottom-surface frame members 121 and the lateral bottom-surface frame members 122 composing the bottom surface 120 are directly provided at the bottom of the suspension member 108 which is widened downwardly. Alternatively, however, it is possible to provide a member connecting both ends of the suspension member 108 downwardly widened, to place the bed bottom on this member, and to suspend it. The bottom surface 120 and the suspension member 108 can be connected by any method as long as the sum of the weights of the bed bottom and the user can be firmly supported. For example, it is possible to employ welding or fastening with bolts and nuts.

The tilt control member 112 is attached to a shoulder of the suspension member 108 via a hinge 109, which is a pin. The hinge 109 makes the rotation of the suspension member 108 smooth. The tilt driving means 112*a* of the tilt control member 112 is connected to a driving energy source (for example, a power supply device) via the lead wires 131 as shown in FIG. 10. The position to fix the tilt control member 112 is not limited to the one shown in FIG. 10. The tilt control member 112 may be composed of a driver for tilting and a holding member for holding the tilt, such as a pin or a brake.

An example in which the columnar mat units 125 are placed on the bottom surface 120 will now be described with reference to FIGS. 13(*a*) and 13(*b*). FIG. 13(*b*) is a cross sectional view taken along arrows A-A of FIG. 13(*a*). As shown in FIGS. 13(*a*) and 13(*b*), the plurality of columnar mat units (bed mat members) 125 having a circular cross section (for example, a diameter of 100 mm) are arranged on the bed bottom surface 120. The columnar mat units 125 are parallel-arranged in the width direction of the bed at intervals of 2 to 20 cm. These units 125 are formed of a mat case which is made of natural rubber and has a hollow filled with polyurethane gel. This material, however, is not the only option available.

When subjected to the user's weight, the cylindrical mat units 125 spread laterally and form a substantially flat surface, which prevents the user lying thereon from feeling uncomfortable such as feeling the surface rough. The mat units compress and rebound unevenly because of their cylindrical shape; the slight movements of the user can provide the user with a massage effect on his/her skin, thereby improving the quality of sleep. In addition, the columnar mat units spaced from each other on the bottom surface can increase the skin massage effect and the air permeability of the bed bottom surface in the upward direction. Thus, the material and the shape of the mat units 125 are preferable in terms of both hygiene and the quality of sleep. To prevent contact with dirt, it is preferable that the surface of the case of the columnar mat units made of natural rubber be covered with a water-repellent film such as a resin film.

However, the material of the columnar mat units is not limited to the above-mentioned one. For example, they can be made of foamed rubber alone without using the mat case. The mat case can be made, for example, of polyethylene. The fluid filled inside can be, for example, gas, liquid material (liquid, gel), powder, or grains. The columnar mat units may be, for example, oval, rectangular, polygonal, or trapezoidal in cross section instead of being circular. It is also possible to use a combination of circular and either rectangular or triangular columnar mat units, or to use those which are different in height or size together.

In the above description, the columnar mat units are placed on the bed bottom surface, which is formed of the bottom board 120'; however, the bottom board may be replaced by a net. It is alternatively possible to place the columnar mat units or other bed mat directly on the bottom support member 123 without using the bottom board 120'.

As described above, in the sleeping-posture-control bed system of the second embodiment, the bed floor portion 102 is suspended by the suspension member 108 so as to be rotatable around the bed-floor support structure 102'. The bed floor portion 102 can be tilted in the lateral direction and be kept at a fixed tilt angle by the tilt control member 112. Thus, the bottom surface 120 on which the user is lying is tilted to induce the user to change his/her posture in bed.

Figure 14:
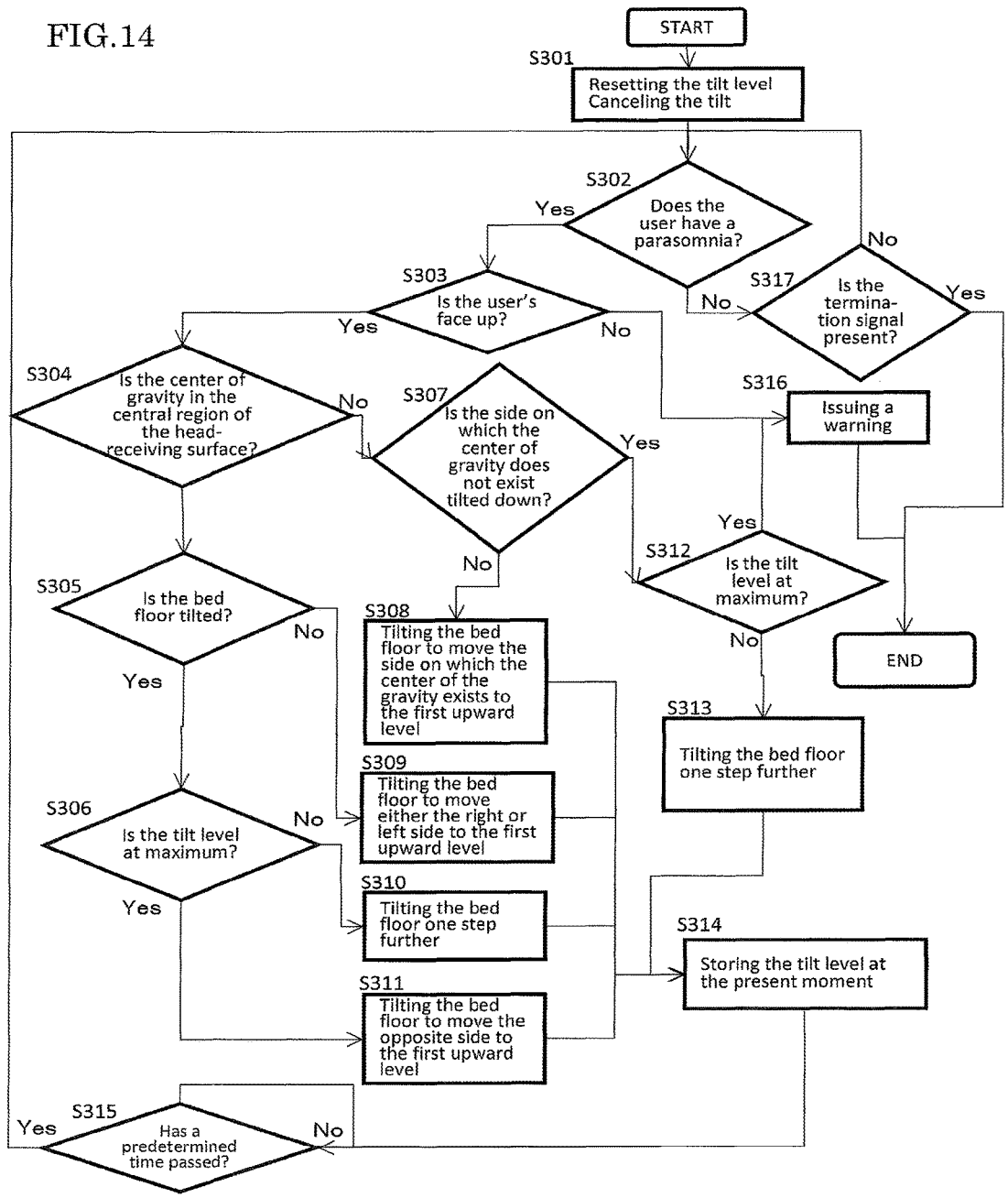
FIG. 14 is a flowchart showing the operation of the sleeping-posture-control bed system of the second embodiment.

The flowchart showing the operation to detect and eliminate parasomnias will now be described with reference to FIG. 14. FIG. 14 is a flowchart showing the operation of the bed system of the second embodiment. In the same manner as in the first embodiment, the present embodiment describes the case of monitoring sleep apnea syndrome as a parasomnia. In the following description, the right and left sides of the bed floor and the user's face correspond to the right and left sides of the user lying face up, and are opposite to the case when the bed floor is seen from above.

The process is started when the power switch is turned on and the presence of the user on the bed floor is detected.

Step S301

In order to start the process from the state in which the bed floor is not tilted (is horizontal), the bed floor is returned to the horizontal position, and the stored tilt level is reset.

Step S302

Next, the parasomnia detector determines the presence or absence of parasomnias from the monitoring information of the sleep monitor. If the user is determined to have parasomnia, the process proceeds to Step S303; otherwise to Step S317. The contents of the determination of the presence or absence of parasomnias (S302) can be the same as those in Steps S201 to S204 (see FIG. 9) of the first embodiment.

Step S303

The tilt driving controller compares the monitoring information of the sleep monitor with information to determine the face direction so that the user's face direction is detected. When the face is up, the process proceeds to Step S304; otherwise to Step S316.

Step S304

The barycentric position detector detects center-of-gravity information. When the center of gravity is in the central region in the lateral direction, the process proceeds to Step S305; otherwise to Step S307.

Step S305

It is determined from the stored tilt level information whether the bed floor is tilted or not at the present moment. When the bed floor is tilted, the process proceeds to Step S306; otherwise to Step S309.

Step S306

It is determined from the stored tilt level information whether the bed floor is tilted to its maximum at the present moment. When it is tilted to its maximum, the process proceeds to Step S311; otherwise to Step S310.

Step S307

The tilt of the bed floor at the present moment is determined when the center of gravity is not in the central region. When the side on which the center of gravity does not exist is tilted down, the process proceeds to Step S312; otherwise to Step S308. The phrase "the side on which the center of gravity does not exist" corresponds to the right region when the head is in the left region, and to the left region when the center of gravity is in the right region.

Step S308

Since the center of gravity is not in the central region, the user is unlikely to fall off the bed even if he/she turns over to the side on which the center of gravity does not exist. Since the side on which the center of gravity does not exist is not tilted down, the bed floor is tilted to move the side on which the center of gravity does not exist to the first downward level. Then, the process proceeds to Step S314.

Step S309

Since the center of gravity is in the central region, and the bed floor is not tilted, the bed floor is tilted to move either the right or left side to the first downward level. Then, the process proceeds to Step S314.

Step S310

Since the center of gravity is in the central region, and the bed floor is tilted less than its maximum, the bed floor is tilted one step further in the same direction. Then, the process proceeds to Step S314.

Step S311

Since the center of gravity is in the central region, and the bed floor is tilted to its maximum, the bed floor is tilted to move the opposite side to the first upward level. Then, the process proceeds to Step S314.

Step S312

It is determined from the stored tilt level information whether the bed floor is tilted to its maximum at the present moment. When it is tilted to its maximum, the process proceeds to Step S313; otherwise to Step S316.

Step S313

Since the center of gravity is in either the right or left region, and the bed floor is tilted less than its maximum, the bed floor is tilted one step further in the same direction. Then, the process proceeds to Step S314.

Step S314

The tilt level at the present moment is stored. Then, the process proceeds to Step S315.

Step S315

If this tilting procedure causes sleep monitoring to be resumed before the user recovers from the abnormal condition, the bed floor may be tilted too much. To avoid this, after the tilting procedure, it is confirmed that a predetermined time has passed before the sleep monitoring is resumed. When the predetermined time has passed, the process returns to Step S302 to continue the sleep monitoring; otherwise Step S315 is repeated. The predetermined time can be set, for example, to five or ten minutes and be stored by a doctor, a nurse, or the like.

Step S316

In this step, parasomnias are present and also the user is in one of the following conditions: (1) the face is not up; and (2) the center of gravity is in either the right or left region of the head-receiving surface, and the side on which the center of gravity does not exist is tiled down to its maximum. These cases indicate that either the user cannot be expected to recover from the parasomnia even if the bed floor is tilted, or the bed floor cannot be tilted any further in the direction to induce the user to turn over. Therefore, a warning is issued to indicate that the user has a parasomnia. The warning can be, for example, directly alerted to the user as warning voice, vibration, etc. or be informed to the helper as warning voice, vibration, warning image, etc.

Step S317

When the parasomnias are absent, it is determined whether the termination signal is present or not. The termination signal is determined to be present when the termination signal switch is turned off or when the user is not detected in bed. When the termination signal is absent, the process proceeds to Step S302 where the presence or absence of the termination signal continues to be detected while the user's parasomnias are continuously monitored. When the termination signal is present, a termination operation is performed.

The second embodiment may employ the process for cancelling the tilt in the same manner as in the modified example of the first embodiment. The present embodiment can also employ a method in which the counter stores tilt conditions as follows: "tilted with the left side up" indicates a negative value; "no tilting" indicates 0; and "tilted with the right side up" indicates a positive value. According to this method, after the tilt is increased, its absolute value can be increased.

As described above, in the present embodiment, the user can be induced to change his/her posture in bed by tilting the bottom surface of the bed floor in the lateral direction. This has the effect of reducing or eliminating parasomnias.

Third Embodiment

Figure 15:
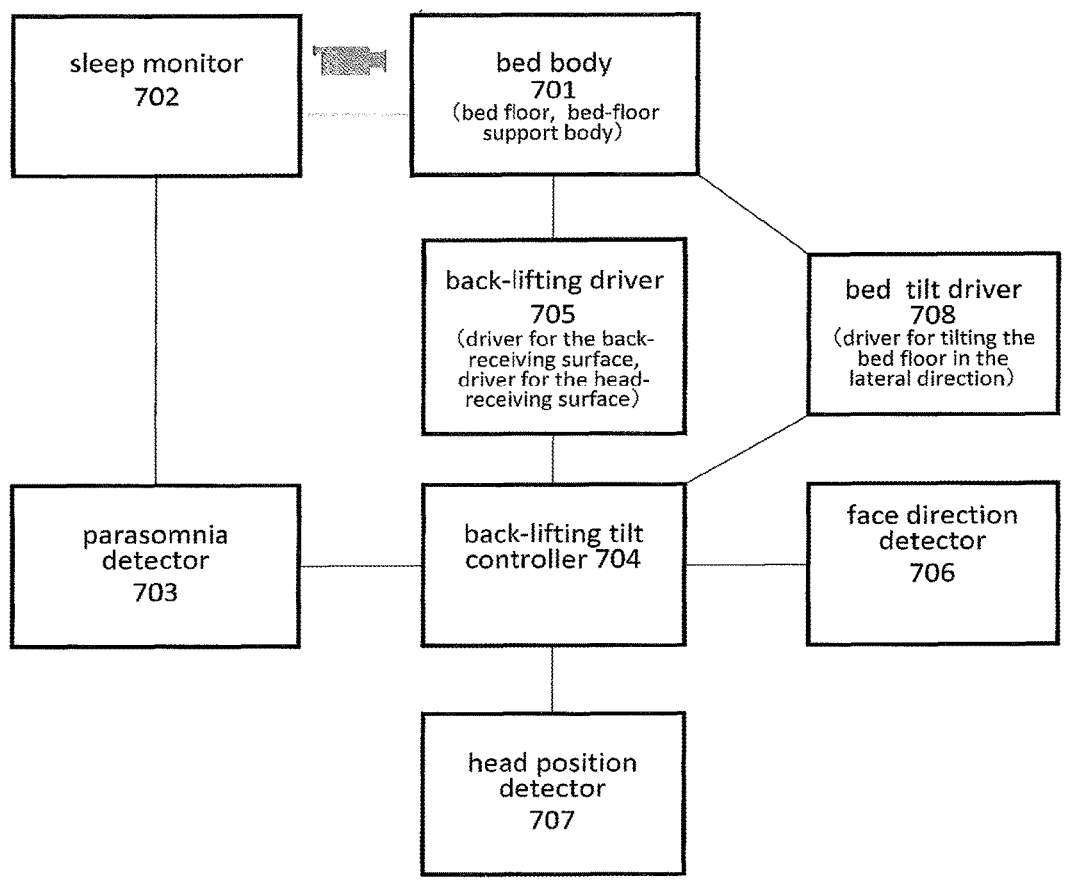
FIG. 15 is a block diagram of the overall structure of the sleeping-posture-control bed system of a third embodiment.

The present embodiment describes a bed system which allows both the tilting of head- and back-receiving surfaces and the lateral tilting of the bed floor. The present embodiment is identical to the first embodiment except that it is essential to control the lateral tilting of the bed floor. Therefore, the description of common aspects (such as the configuration of the bed body) will be omitted. FIG. 15 is a block diagram of the overall structure of the sleeping-posture-control bed system of the third embodiment.

The present embodiment has the same configuration as the first embodiment described with FIG. 6 except that it includes a bed-floor tilt driver 708 as an essential component. The bed-floor tilt driver 708 is a driver for tilting the bed floor of the bed body 701 in the lateral direction. The user can be induced to change his/her posture in bed by tilting the bed floor in the lateral direction. The bed-floor tilt driver 708 is composed, for example of the driver 26 for tilting the bed floor in the lateral direction (see FIG. 1), which rotates the bed floor around the rotary shaft pin 14 as shown in FIG. 1.

A back-lifting tilt controller 704 determines the tilt angles of the back- and head-receiving surfaces and the tilt angle of the bed floor in the lateral direction on the basis of the monitoring data of a sleep monitor 702 and detection information from a head position detector 707 and from a face direction detector 706. The back-lifting tilt controller 704 then tilts the back- and head-receiving surfaces and the bed floor. The tilt angle θx of the back-receiving surface, the tilt angle θy of the head-receiving surface, and the tilt angle of the bed floor in the lateral direction at some time point may be stored in the memory of the back-lifting tilt controller 704. Alternatively, each of the tilt angles of the back- and head-receiving surfaces and the tilt angle of the bed floor in the lateral direction may be divided into multiple steps, and the tilt step number of each of these surfaces and the tilt level number of the bed floor in the lateral direction may be stored in a counter formed in the back-lifting tilt controller 704.

Figure 16:
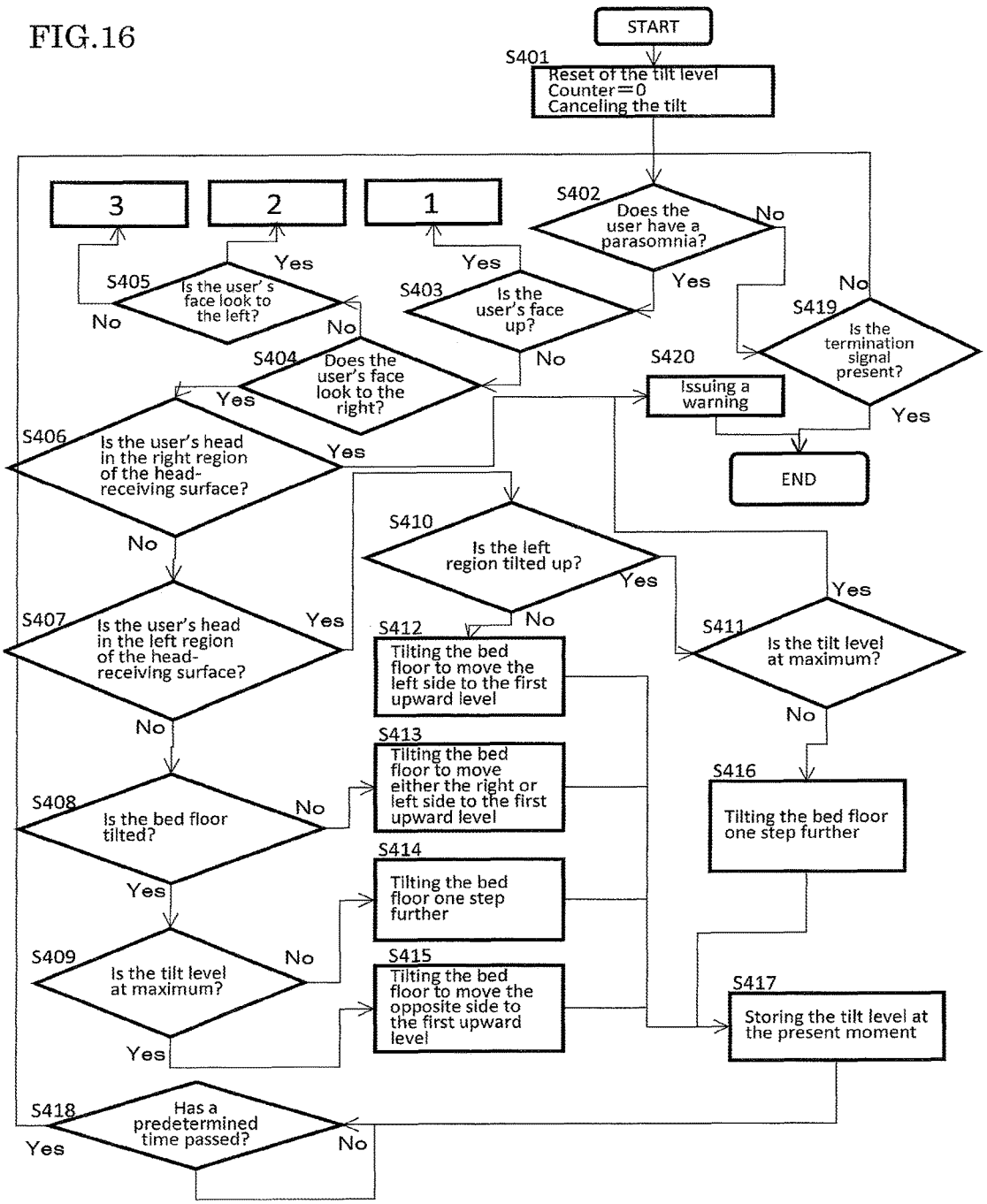
FIG. 16 is a flowchart showing an operation of the sleeping-posture-control bed system of the third embodiment.
Figure 17:
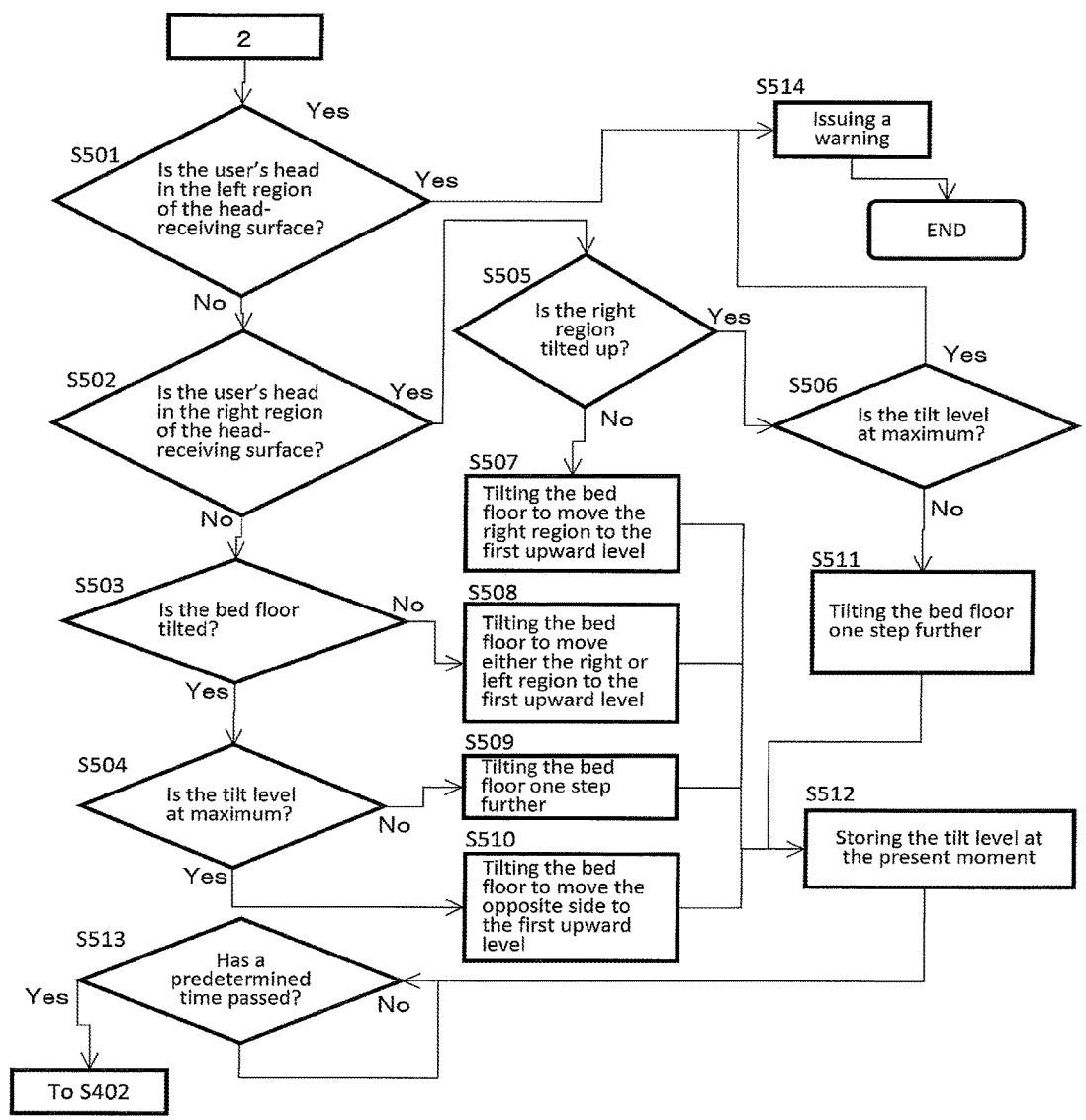
FIG. 17 is a flowchart showing operation 2 of the sleeping-posture-control bed system of the third embodiment.
Figure 18:
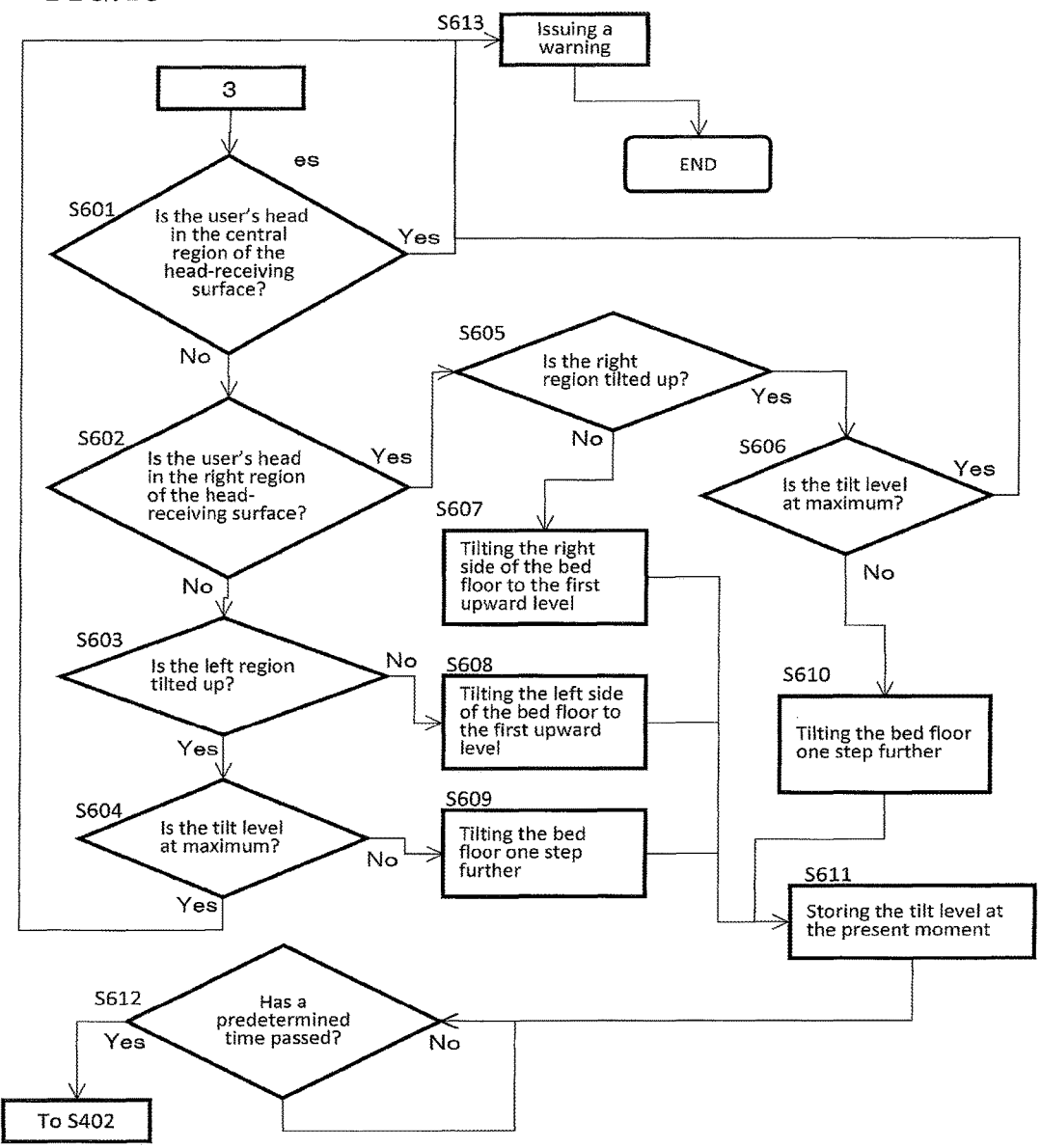
FIG. 18 is a flowchart showing operation 3 of the sleeping-posture-control bed system of the third embodiment.

The following is a description of the process for tilting the head- and back-receiving surfaces preferentially over the lateral tilting of the bed floor. FIGS. 16 to 18 show flowchart showing the operation of the sleeping-posture-control bed system of the third embodiment.

In FIG. 16, the process is started when the power switch is turned on and the presence of the user on the bed floor is detected.

Step S401

In order to start the process from the state in which none of the back- and head-receiving surfaces and the bed floor are tilted, the stored tilt level (in the lateral direction) is reset, and the counter to store the tilts of the back- and head-receiving surfaces is reset to 0 so as to cancel the tilts.

Step S402

Next, the parasomnia detector determines the presence or absence of parasomnias from the monitoring information of the sleep monitor. If the user is determined to have parasomnia, the process proceeds to Step S403; otherwise to Step S419.

Step S403 to S405

The face direction detector determines the user's face direction from the information of the head position detector. When the face is up, the process is followed by a process represented by reference numeral 1. When the face looks to the right, the process proceeds to Step S406. When the face looks to the left, the process is followed by a process represented by reference numeral 2. When the face is in none of them (down), the process is followed by a process represented by reference numeral 3.

Steps S406 and S407

The head position detector detects the head position on the head-receiving surface (see FIG. 6). When the head is in the right region in the lateral direction, the process proceeds to Step S420 to issue a warning. When the head is in the left region in the lateral direction, the process proceeds to Step S410. When the head is in neither of them (the head is in the central region in the lateral direction), the process proceeds to Step S408.

Step S408

It is determined from the stored tilt level information whether the bed floor is tilted or not at the present moment. When the bed floor is tilted, the process proceeds to Step S409; otherwise to Step S413.

Step S409

It is determined from the stored tilt level information whether the bed floor is tilted to its maximum at the present moment. When it is tilted to its maximum, the process proceeds to Step S415; otherwise to Step S414.

Step S410

The tilt of the bed floor at the present moment is determined when the head is in the left region in the lateral direction. When the left region of the bed floor is tilted up, the process proceeds to Step S411; otherwise to Step S412.

Step S411

It is determined from the stored tilt level information whether the bed floor is tilted to its maximum at the present moment. When it is tilted to its maximum, the process proceeds to Step S420; otherwise to Step S416.

Step S412

The left region of the bed floor is tilted to the first upward level. Then, the process proceeds to Step S417.

Step S413

Either the right or left region of the bed floor is tilted to the first upward level. Then, the process proceeds to Step S417.

Step S414

Since the tilt is not at its maximum, the bed floor is tilted one step further. Then, the process proceeds to Step S417.

Step S415

Since the user's head is in the central region, and the bed floor is tilted to its maximum, the bed floor is tilted to move the opposite side to the first upward level. Then, the process proceeds to Step S417.

Step S416

Since the tilt is not at its maximum, the bed floor is tilted one step further. Then, the process proceeds to Step S417.

Step S417

The tilt level at the present moment is stored. Then, the process proceeds to Step S418.

Step S418

If this tilting procedure causes sleep monitoring to be resumed before the user recovers from the abnormal condition, the bed floor may be tilted too much. To avoid this, after the tilting procedure, it is confirmed that a predetermined time has passed before the sleep monitoring is resumed. When the predetermined time has passed, the process returns to Step S402 to continue the sleep monitoring; otherwise Step S418 is repeated. The predetermined time can be set, for example, to five or ten minutes and be stored by a doctor, a nurse, or the like.

Step S419
When the parasomnias are absent, it is determined whether the termination signal is present or not. The termination signal is determined to be present when the termination signal switch is turned off or when the user is not detected in bed. When the termination signal is absent, the process proceeds to Step S402 where the presence or absence of the termination signal continues to be detected while the user's parasomnias are continuously monitored. When the termination signal is present, a termination operation is performed.

Step S420
In this step, parasomnias are present and also the user is in one of the following conditions: (1) the face is not up; and (2) the head is in either the right or left region of the head-receiving surface, and the region opposite to the region on which the head is located is tilted down to its maximum. These cases indicate that either the user cannot be expected to recover from the parasomnia even if the bed floor is tilted, or the bed floor cannot be tilted any further in the direction to induce the user to turn over. Therefore, a warning is issued to indicate that the user has a parasomnia. The warning can be, for example, directly alerted to the user as warning voice, vibration, etc. or be informed to the helper as warning voice, vibration, warning image, etc.

Process Represented by Reference Numeral 1
Since the user's face is up, the same operation as in Step S104 to S109 and the termination operation in the first embodiment are performed; hence, the description thereof is omitted. The shift from Step S108 to Step S102 corresponds to the shift from Step 108 to Step S402.

Process Represented by Reference Numeral 2
This process is shown in FIG. 17. Since the user's face is tilted to the left, the process in Steps S501 to S514 is opposite in the user's face direction to the process in Steps S406 to S418 and S420 in which the user's face is tilted to the right. Therefore, the description thereof is omitted.

Process Represented by Reference Numeral 3
This process is shown in FIG. 18. In this case, the user's face is down. In this case, opposite to the case described above, when the user's head is in the central region, the user may fall off the bed if he/she is turned over upward.

Steps S601 and S602
The head position on the head-receiving surface is detected. When the head is in the right region in the lateral direction, the process proceeds to Step S605, whereas when the head is in the left region in the lateral direction, the process proceeds to Step S603. When the head is in neither of them (the head is in the central region in the lateral direction), the process proceeds to Step S613.

Step S603
The tilt of the bed floor at the present moment is determined from the stored tilt level information. When the left region of the bed floor is tilted up, the process proceeds to Step S604; otherwise to Step S608.

Step S604
It is determined from the stored tilt level information whether the bed floor is tilted to its maximum at the present moment. When it is tilted to its maximum, the process proceeds to Step S613; otherwise to Step S609.

Step S605
The tilt of the bed floor at the present moment is determined from the stored tilt level information. When the right region of the bed floor is tilted up, the process proceeds to Step S606; otherwise to Step S607.

Step S606
It is determined from the stored tilt level information whether the bed floor is tilted to its maximum at the present moment. When it is tilted to its maximum, the process proceeds to Step S613; otherwise to Step S610.

Step S607
The right region of the bed floor is tilted to the first upward level. Then, the process proceeds to Step S611.

Step S608
The left region of the bed floor is tilted to the first upward level. Then, the process proceeds to Step S611.

Step S609
Since the tilt is not at its maximum, the bed floor is tilted one step further. Then, the process proceeds to Step S611.

Step S610
Since the tilt is not at its maximum, the bed floor is tilted one step further. Then, the process proceeds to Step S611.

Step S611
The tilt level at the present moment is stored. Then, the process proceeds to Step S612.

Step S612
If the tilting procedure causes sleep monitoring to be resumed before the user recovers from the abnormal condition, the bed floor may be tilted too much. To avoid this, after the tilting procedure, it is confirmed that a predetermined time has passed before the sleep monitoring is resumed. When the predetermined time has passed, the process returns to Step S402 to leave the process represented by reference numeral 3.

Step S613
In this step, parasomnias are present, and also the user's head is down and is in one of the following conditions: (1) the head is in the central region of the head-receiving surface in the lateral direction; and (2) the head is in either the right or left region of the head-receiving surface, and the side opposite to the side on which the head is located is tilted to its maximum. These cases indicate that either the user cannot be expected to recover from the parasomnia even if the bed floor is tilted, or the bed floor cannot be tilted any further in the direction to induce the user to turn over. Therefore, a warning is issued to indicate that the user has a parasomnia. The warning can be, for example, directly alerted to the user as warning voice, vibration, etc. or be informed to the helper as warning voice, vibration, warning image, etc.

The third embodiment may employ the process for cancelling the tilt in the same manner as in the modified example of the first embodiment. Furthermore, the lateral tilting of the bed floor may be reset before tilting the back-receiving surface and the head-receiving surface.

The following is a description of how to determine the presence or absence of parasomnias. This determination is performed using $CO_2$ concentration, which is increased by respiration.

In this case, the parasomnia detector 503 includes a $CO_2$ concentration sensor and a detector for detecting the presence or absence of abnormal respiration (hypopnea or apnea) by comparing data of the $CO_2$ concentration sensor and a predetermined threshold. The term "apnea" means that the airflow through mouth and nose stops for ten seconds or more, whereas the term "hypopnea" means that the ventilation rate decreases by 50% or more for ten seconds or more. The predetermined threshold can be determined from the user's sleep data or standard data by a doctor, a nurse, or the like.

The sleep monitor 502 can further include a CO$_2$ concentration sensor and a communication unit for sending monitoring data to the parasomnia detector 503.

The CO$_2$ concentration sensor is disposed near at least one of the nose or mouth of the user, but may be disposed near both of them.

Fourth Embodiment

Figure 19:
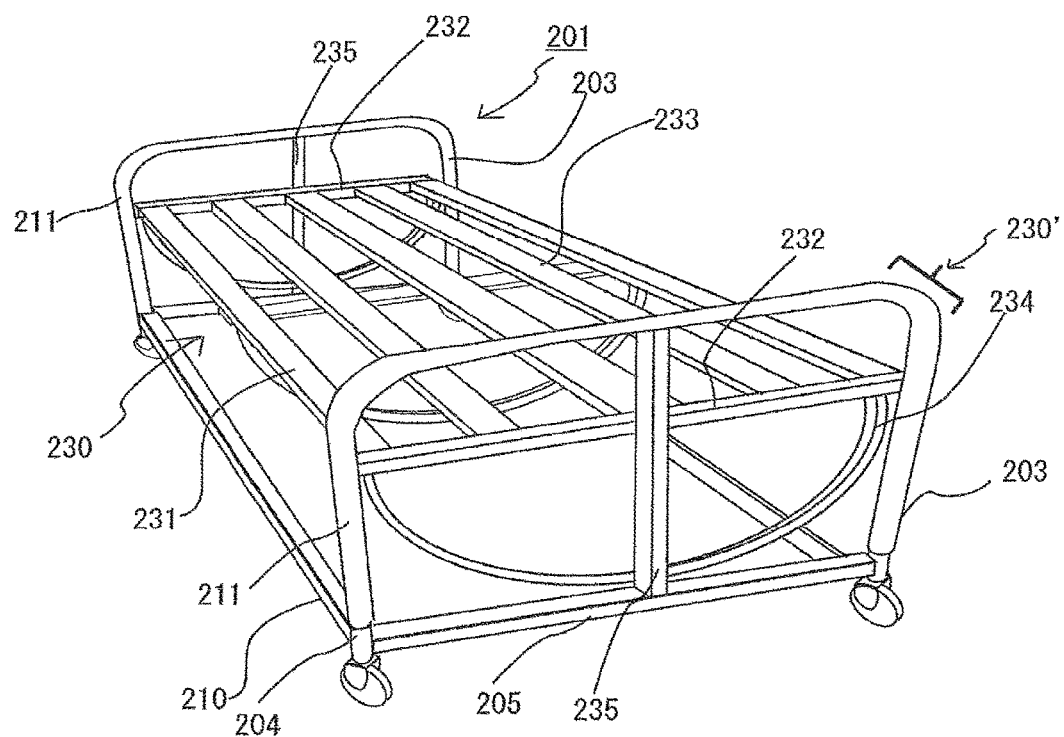
FIG. 19 is a perspective view of a bed body of a sleeping-posture-control bed system of a fourth embodiment.

The bed body of a sleeping-posture-control bed system of the fourth embodiment is shown in FIG. 19. As shown in FIG. 19, the bed system of the fourth embodiment includes a bed floor portion 230 composed of longitudinal frame members 231, lateral frame members 232, and semicircular members 234. The bed floor portion 230 having a bottom surface 233 is attached rotatably (in a tiltable manner) to vertical frames 235 of stand frames 211. The overall structure of the present embodiment is similar to that shown in FIG. 11.

The bed-floor tilt driver (a tilting means for tilting the bottom surface 233) of the bed system may have the following structures. As one example, the semicircular members 234 each have grooves to mesh with a gear on their inner or outer periphery, and the gear is disposed near the bottom end of each of the semicircular members 234 and is driven by an electric motor. As another example, a rotational bearing is disposed near the intersection between the two vertical frames 235 and the longitudinal center line of the bottom surface 233, and the bed floor portion 230 is provided with a shaft, which is inserted in the rotational bearing and driven by an electric motor. In the latter example, the semicircular members 234 are equipped with brakes (the holding member of the bed-floor tilt driver) by which the bed floor portion 230 is fixed to a bed-floor support structure 230' while the bed floor portion 230 is being tilted. The ON and OFF of the fixed engagement by the brakes is automatically controlled by the bed-floor tilt driver.

The above-mentioned electric motors are connected to a controller (not shown) similar to the operating unit described in the second embodiment (including the parasomnia detector, the tilt driving controller, and the barycentric position detector). The controller controls the electric motor. This, however, is not the only configuration available. What matters is that the tilt driving controller can tilt the bottom surface 233 smoothly and keep it tilted on the basis of information from any of the sleep monitor, the parasomnia detector, and the barycentric position detector.

The barycentric position detector is a dispensable component. For simplification, FIG. 19 omits the sleep monitor, the holding member (brakes) of the bed-floor tilt driver, and the columnar mat units on the bottom surface of the bed body.

This configuration provides effects similar to those in the second embodiment.

Fifth Embodiment

Figure 20:
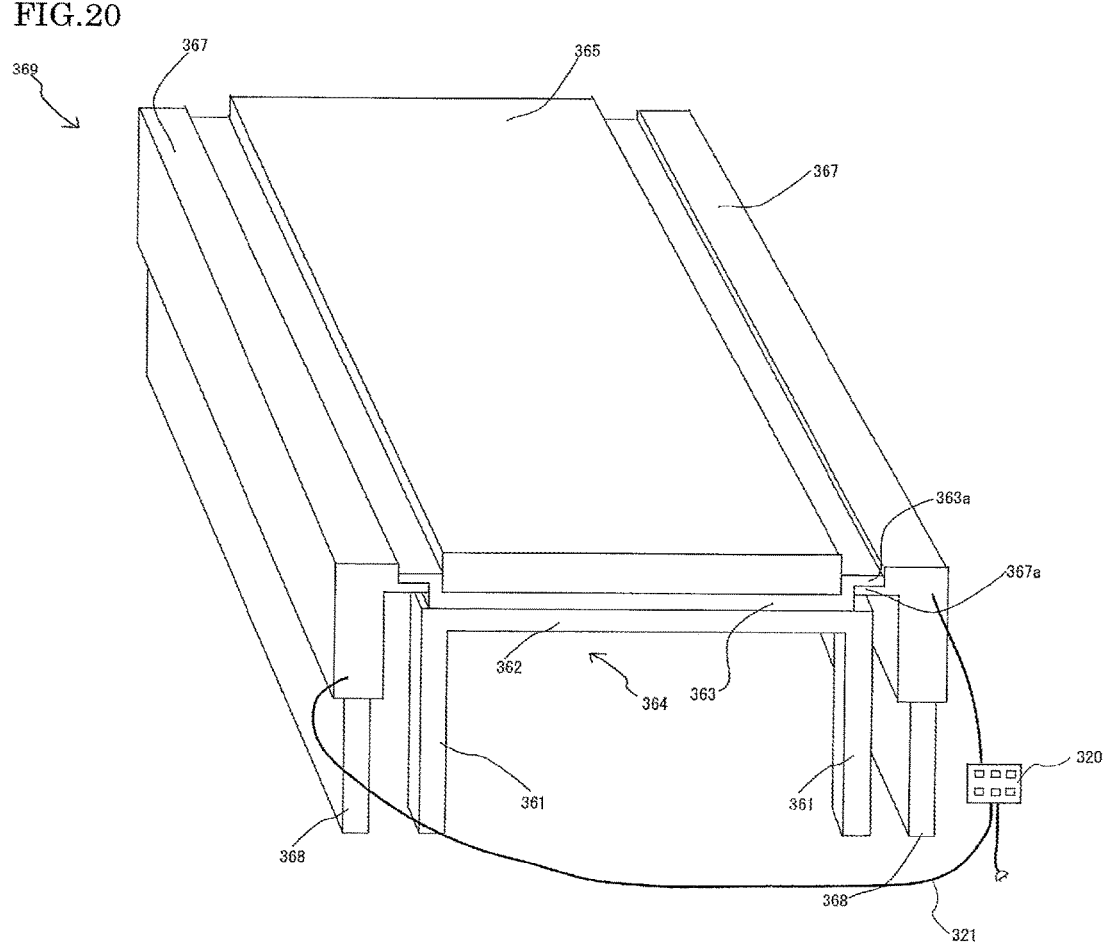
FIG. 20 is a front perspective view of a bed body of a sleeping-posture-control bed system of a fifth embodiment.

A sleeping-posture-control bed system of a fifth embodiment includes a bed body and a bed-floor tilt driver shown in FIG. 20. FIG. 20 is a perspective view of the bed body. As shown in FIG. 20, the bed system of the fifth embodiment includes a bed bottom support 369. The bed bottom support 369 has lift mechanism 367 for holding a bed floor portion 363 having a bottom surface and tilting the bed floor portion 363. The bed system further includes a bed mat support 364, which supports the bed bottom support 369 from below; and a bed mat 365 held on the bed floor portion 363. In the present embodiment, the upper surface of the bed floor portion 363 corresponds to the bottom surface of the bed body. The lift mechanism 367 functions as a bed-floor tilt driver for tilting the bottom surface in the lateral direction.

The lift mechanism 367 is connected via a lead wire 321 to a controller 320, which is similar to the operating unit (including the parasomnia detector, the tilt driving controller, and the barycentric position detector) described in the second embodiment. The controller 320 detects parasomnias and the position of the center of gravity and also controls the lift mechanism 367.

The bed bottom support 369 includes the lift mechanism (bed-floor tilt driver) 367 for tilting the bed floor portion 363, and foot parts 368 supporting the lift mechanism 367. At the ends of the lift mechanism 367 and both ends of the bed floor portion 363 are provided engaging portions 367a and 363a which engage the bed floor portion 363 with the lift mechanism 367. FIG. 20 does not illustrate the sleep monitor.

The bed mat support 364 includes a bottom support 362 to support the bed floor portion 363, and foot parts 361 to support the bottom support 362.

The bed system with the above-described configuration operates as follows. In FIG. 20, for example, when the lift mechanism 367 moves up on the right side and moves down on the left side, the bed floor portion 363 is tilted up on the right side. When the lift mechanism 367 is operated oppositely, the bed floor portion 363 is tilted up on the left side. The lift mechanism 367 is controlled by the operating unit in the same manner as in the second embodiment. The lift mechanism can be any of well-known devices such as a hydraulic device.

This configuration also provides effects similar to those in the second embodiment.

Sixth Embodiment

Figure 21:
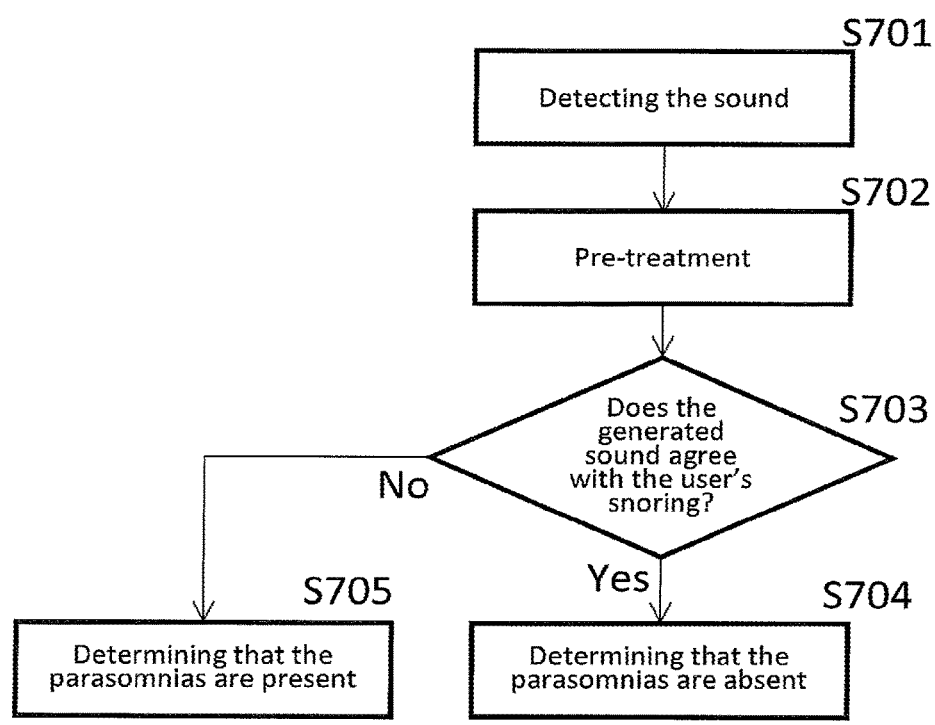
FIG. 21 is a flowchart of the determination of the presence or absence of parasomnias by a sleeping-posture-control bed system of a sixth embodiment.

A sixth embodiment describes a sleeping-posture-control bed system that can determine the presence or absence of the user's snoring by means of sound, and can eliminate the snoring. The present embodiment is identical to the second embodiment except for an abnormality determination process performed by the parasomnia detector; hence, the following description will be focused on the abnormality determination process. FIG. 21 is a flowchart of the determination of the presence or absence of parasomnias by the bed system of the sixth embodiment.

Step S701

When the operation is started, first of all, the sound sensor monitors the sound generated around the user's mouth.

Step S702

In order to facilitate the determination, pre-treatment such as denoising and Fourier transformation are performed.

Step S703

The data obtained by pre-treatment of the user's snoring is stored in the parasomnia detector. The parasomnia detector compares the measured sound data with the stored data. When the degree of agreement between these data is not less than a predetermined value (for example, 80%), the process proceeds to Step S704; otherwise to Step S705. Note that when the degree of agreement is less than the predetermined value, it may be the case that no sound has been detected.

Step S704

When the degree of agreement is not less than the predetermined value, it means that the user is snoring, and the parasomnias are determined to be present.

Step S705

When the degree of agreement is less than the predetermined value, the user is not snoring, and the parasomnias are determined to be absent.

A determination based on the flow rate can be performed in the same manner as in Steps S201 to S204, and a determination based on the vibration can be determined in the same manner as in Steps S701 to S705.

Seventh Embodiment

Figure 22:
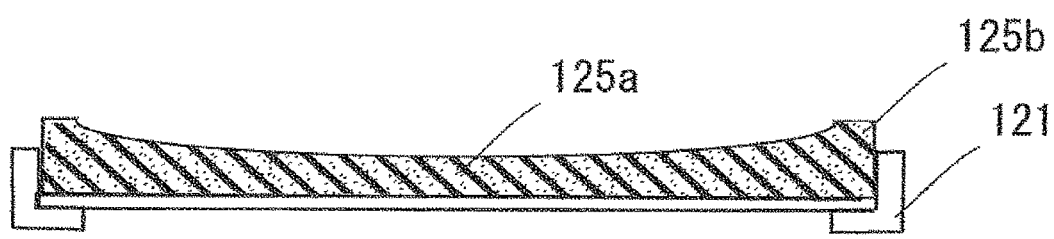
FIG. 22 is a cross sectional view of a bed mat of a modified example in a sleeping-posture-control bed system of a seventh embodiment.

A seventh embodiment will describe a bed mat structure that prevents the user from falling off the bed. The present embodiment is identical to the second embodiment except for the bed mat structure; hence, the following description will be focused on the difference. FIG. 22 is a transverse cross sectional view of the bed mat of the seventh embodiment.

In the present embodiment, as shown in FIG. 22, the bed mat 125 has a central portion 125a, which is in the form of a recess lower than both end portions 125b. The end portions 125b function to prevent the user from falling off the bed when the bed bottom surface is tilted.

It is preferable that the width of the central portion 125a be not less than 80% of the total width of the bed mat, and that the width of each of the end portions 125b be not less than 3% of the total width of the bed mat.

In the present embodiment, the recess is semioval in cross section, but is not limited to this: it can alternatively be for example, arc- or catenary-shaped.

Eighth Embodiment

Figure 23:
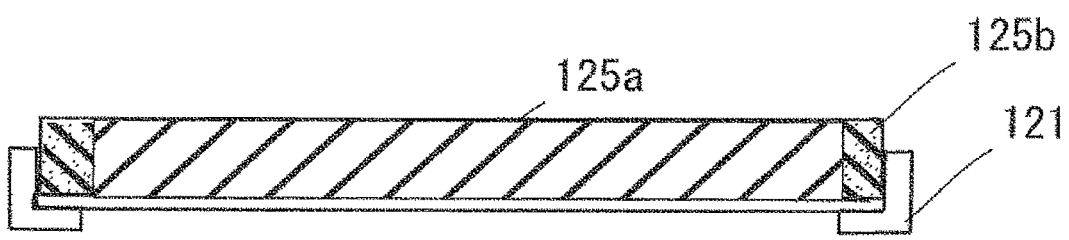
FIG. 23 is a cross sectional view of a bed mat of a modified example in a sleeping-posture-control bed system of an eighth embodiment.

An eighth embodiment will describe a modified example of the bed mat structure that prevents the user from falling off the bed. The present embodiment is identical to the second embodiment except for the bed mat structure; hence, the following description will be focused on the difference. FIG. 23 is a transverse cross sectional view of the bed mat of the eighth embodiment.

In the present embodiment, as shown in FIG. 23, the material of the bed mat 125 differs between the central portion 125a and the end portions 125b. More specifically, the material for the central portion 125a has a higher compressibility than the material for the end portions 125b. Therefore, when the user lies on it, the central portion 125a sinks deep, whereas the end portions 125b hardly sink. Thus, the end portions 125b with little compressibility function to prevent the user from falling off the bed.

The bed mat structures of the seventh and eighth embodiments are applicable to the bed system of the first embodiment. In that case, a columnar bed mat is placed in such a manner as not to inhibit the bending of the head- and back-receiving surfaces.

INDUSTRIAL APPLICABILITY

As described above, the present invention provides a bed system capable of being tilted in multiple directions. The bed system can tilt its bottom surface regularly, discontinuously, or whenever necessary so as to prevent a bedridden patient from developing pressure ulcers. The bed system can also detect parasomnias of the user, such as apnea, hypopnea, snoring, and teeth grinding, and upon detection of a parasomnia, induce the user to change his/her sleeping posture so as to reduce the parasomnia. Thus, the present invention provides high industrial applicability.

REFERENCE MARKS IN THE DRAWINGS 1 sleeping-posture-control bed system
10 bed body
11 operating unit
12 head frame
13 foot frame
14 rotary shaft pin
15 suspension member
16 back-receiving surface portion
17 head-receiving surface portion
18 driver for the back-receiving surface
19 driver for the head-receiving surface
20 waist-receiving surface portion
21 knee bending driver
22 driver for vertically moving the bed floor
23 driver for vertically moving the bed floor
24 upper-leg-receiving surface portion
25 lower-leg-receiving surface portion
26 driver for tilting the bed floor in the lateral direction
27 longitudinal frame member
28 lateral frame member
29 head-foot connecting member
30 foot part
31 lead wire
32 reinforcing member
33 roller
35 body central axis
36 pressure-sensitive sheet
37 connecting member
102 bed floor portion
102' bed-floor support structure
103 stand frame
104 foot part
105 foot-foot connecting frame
106 stand connecting frame
107 vertically movable frame
107a vertically driving means
108 suspension member
109 hinge
110 head-foot connecting member
112 tilt control member
112a tilt driving means
115 handrail
120 bottom surface
120' bottom board
121 longitudinal bottom-surface frame member
122 lateral bottom-surface frame member
123 bottom support member
125 cylindrical mat unit
130 operating unit
131 lead wire
211 stand frame
230 bed floor portion
231 longitudinal frame member
232 lateral frame member
233 bottom surface
234 semicircular member
235 vertical frame
361 foot part
362 bottom support
363 bed floor portion
364 bed mat support
365 bed mat
367 lift mechanism (bed-floor tilt driver)
368 foot part
369 bed bottom support
501 bed body
502 sleep monitor
503 parasomnia detector
504 tilt driving controller
505 bed-floor tilt driver
506 barycentric position detector
602 back-receiving-surface longitudinal frame
602a back-receiving-surface longitudinal main member
602b back-receiving-surface longitudinal elastic member 603 rotary rod
604 motor
605, 606 longitudinal reinforcing member

The invention claimed is:
1. A sleeping-posture-control bed system comprising:
   a bed floor including a back-lifting portion configured to lift a user's back, the back-lifting portion including a back-receiving surface and a head-receiving surface, each of the back-receiving surface and the head-receiving surface being capable of tilting upward and downward and being adjusted at different tilt angles;
   a bed-floor support body supporting the bed floor;
   a head detector configured to detect whether the user's head is located on the head-receiving surface; and
   a back-lifting driver configured to tilt the back-receiving surface and the head-receiving surface, the back-lifting driver not tilting up the back-receiving surface or the head-receiving surface when the head detector does not detect that the user's head is located on the head-receiving surface.
2. The sleeping-posture-control bed system according to claim 1 further comprising:
   a sleep monitor configured to monitor sleep of the user lying on the bed floor;
   a parasomnia detector configured to detect a presence or absence of a parasomnia on a basis of monitoring data acquired by the sleep monitor; and
   a tilt driving controller configured to control the bed-floor tilt driver on a basis of a detection result of the parasomnia detector in such a manner that the bed floor is tilted.
3. The sleeping-posture-control bed system according to claim 2, further comprising a bed-floor tilt driver configured to tilt the bed floor in a longitudinal direction and in a lateral direction of the bed floor.
4. The sleeping-posture-control bed system according to claim 3, further comprising a bed mat to be placed on the bed floor, the bed mat having a higher compressibility at a central portion in a width of the bed mat than at both end portions in the width of the bed mat.
5. The sleeping-posture-control bed system according to claim 3, further comprising a bed mat to be placed on the bed floor, the bed mat having a shape recessed from both ends of a width of the bed mat toward a center of the bed mat along a length of the bed floor.
6. The sleeping-posture-control bed system according to claim 3, further comprising a bed mat to be placed on the bed floor, the bed mat being recessed in a form of an elliptic arc in a cross section perpendicular to a length of the bed floor.
7. A sleeping-posture-control bed system comprising:
   a bed floor including a back-lifting portion configured to lift a user's back, the back-lifting portion including a back-receiving surface and a head-receiving surface, each of the back-receiving surface and the head-receiving surface being capable of tilting upward and downward independently and being adjusted at different tilt angles;
   a bed-floor support body supporting the bed floor;
   a back-lifting driver configured to tilt up a head side of the back-lifting portion;
   a bed-floor tilt driver configured to tilt the bed floor in a longitudinal direction and in a lateral direction of the bed floor;
   a sleep monitor configured to monitor sleep of the user sleeping on the bed floor;
   a parasomnia detector configured to detect a presence or absence of a parasomnia on a basis of monitoring data acquired by the sleep monitor; and
   a tilt driving controller configured to control the bed-floor tilt driver on a basis of a detection result of the parasomnia detector so that the bed floor is tilted.
8. The sleeping-posture-control bed system according to claim 7, further comprising a center-of-gravity position detector configured to detect a user's center of gravity,
   wherein if a projection point corresponding to the user's center of gravity on the bed floor at a time when the parasomnia detector detects the presence of the parasomnia is located lower in a tilt direction of the bed floor than a center line of the bed floor, the center line being perpendicular to the tilt direction and including a center point of an area of the bed floor, the tilt driving controller makes the bed-floor tilt driver tilt up the bed floor so that the projection point is located higher than the center line of the bed floor.
9. The sleeping-posture-control bed system according to claim 7, further comprising a face direction detector configured to detect whether the user's face is up, tilted to the right, tilted to the left, or down with respect to the head-receiving surface.
10. The sleeping-posture-control bed system according to claim 9, further comprising a back-lifting tilt controller configured to determine a tilt angle of at least one of the back-receiving surface and the head-receiving surface, and a tilt direction and a tilt angle of the bed floor on the basis of the detection result of the parasomnia detector and face direction information obtained from the face direction detector so as to drive the back-lifting driver and/or the bed-floor tilt driver to the determined tilt angles.
11. The sleeping-posture-control bed system according to claim 7, further comprising a bed mat to be placed on the bed floor, the bed mat having a higher compressibility at a central portion in a [lateral direction] width of the bed mat than at both end portions in the [lateral direction] width of the bed mat.
12. The sleeping-posture-control bed system according to claim 7, further comprising a bed mat to be placed on the bed floor, the bed mat having a shape recessed from both ends of a width of the bed mat toward a center of the bed mat along a length of the bed floor.
13. The sleeping-posture-control bed system according to claim 7, further comprising a bed mat to be placed on the bed floor, the bed mat being recessed in a form of an elliptic arc in a cross section perpendicular to a length of the bed floor.
14. A sleeping-posture-control bed system comprising:
   a bed floor including a back-lifting portion configured to lift a user's back, the back-lifting portion including a back-receiving surface and a head-receiving surface, each of the back-receiving surface and the head-receiving surface being capable of tilting upward and downward and being adjusted at different tilt angles;
   a bed-floor support body supporting the bed floor; and
   a back-lifting driver configured to tilt the back-receiving surface and the head-receiving surface within a range of satisfying Mathematical Formula (1) such that the user's posture is changed without increasing a pressure of blood flow into the user's head,

$$0° < \theta x \leq \zeta°, -45° \leq \theta y < 0°, \text{ and } 0° \leq \theta x + \theta y \quad (1)$$

where
$\theta x$ is a tilt angle of the back-receiving surface lifted from 0° at which the back-receiving surface is in an unlifted position; and θy is a tilt angle of the head-receiving surface when the back-receiving surface is at the tilt angle of θx and an extended line of the back-receiving surface is referred to as 0°.

15. The sleeping-posture-control bed system according to claim 14, further comprising:
   a sleep monitor configured to monitor sleep of the user lying on the bed floor;
   a parasomnia detector configured to detect a presence or absence of a parasomnia on a basis of monitoring data acquired by the sleep monitor; and
   a back-lifting tilt controller configured to determine a value of θx and a value of θy on a basis of a detection result of the parasomnia detector and configured to drive the back-lifting driver such that the value of θx and the value of θy satisfy the Mathematical Formula (1).

16. The sleeping-posture-control bed system according to claim 14, further comprising:
   a sleep monitor configured to monitor sleep of the user lying on the bed floor;
   a parasomnia detector configured to detect a presence or absence of a parasomnia on a basis of monitoring data acquired by the sleep monitor;
   a bed-floor tilt driver configured to tilt the bed floor; and
   a back-lifting tilt controller configured to perform following operations:
      to determine a value of θx and a value of θy on a basis of a detection result of the parasomnia detector;
      to determine a tilt direction and a tilt angle of the bed floor; and
      to drive the back-lifting driver and/or the bed-floor tilt driver so as to achieve the value of θx, the value of θy, the tilt direction, and the tilt angle.

17. The sleeping-posture-control bed system according to claim 14, further comprising:
   a head detector having a function of detecting in which region of the head-receiving surface the user's head is located;
   a face direction detector configured to detect whether the user's face is up, tilted to a right, tilted to a left, or down with respect to the head-receiving surface;
   a bed-floor tilt driver configured to tilt the bed floor; and
   a back-lifting tilt controller configured to determine a tilt direction and a tilt angle of the bed floor on a basis of information about a location of the user's head obtained from the head detector and information about a direction of the user's face obtained from the face direction detector, and configured to drive the bed-floor tilt driver in such a manner as to achieve the tilt direction and the tilt angle of the bed floor.

18. The sleeping-posture-control bed system according to claim 14, further comprising:
   a sleep monitor configured to monitor sleep of the user lying on the bed floor;
   a parasomnia detector configured to detect a presence or absence of a parasomnia on a basis of monitoring data acquired by the sleep monitor;
   a center-of-gravity position detector configured to detect the user's center of gravity;
   a bed-floor tilt driver configured to tilt the bed floor; and
   a tilt driving controller configured to perform following operations:
      to receive information about the user's center of gravity from the center-of-gravity position detector;
      to detect a difference in the user's center of gravity on the bed floor between when the parasomnia detector has determined the presence of a parasomnia and when the bed floor has been tilted; and
      to drive the bed-floor tilt driver in a direction to reduce the tilt of the bed floor when the difference exceeds a threshold.

* * * * *

UNITED STATES PATENT AND TRADEMARK OFFICE
CERTIFICATE OF CORRECTION

PATENT NO. : 9,907,716 B2  
APPLICATION NO. : 15/589407  
DATED : March 6, 2018  
INVENTOR(S) : Toshiko Miyashita et al.

Page 1 of 2

It is certified that error appears in the above-identified patent and that said Letters Patent is hereby corrected as shown below:

In the Claims

Column 39 Lines 23-33 in Claim 2 change:
2. The sleeping-posture-control bed system according to claim 1 further comprising:
　　a sleep monitor configured to monitor sleep of the user lying on the bed floor;
　　a parasomnia detector configured to detect a presence or absence of a parasomnia on a basis of monitoring data acquired by the sleep monitor; and
　　a tilt driving controller configured to control the bed-floor tilt driver on a basis of a detection result of the parasomnia detector in such a manner that the bed floor is tilted.
To be:
2. The sleeping-posture-control bed system according to claim 1, further comprising:
　　a sleep monitor configured to monitor sleep of the user lying on the bed floor;
　　a parasomnia detector configured to detect a presence or absence of a parasomnia on a basis of monitoring data acquired by the sleep monitor; and
　　a tilt driving controller configured to control the bed-floor tilt driver on a basis of a detection result of the parasomnia detector in such a manner that the bed floor is tilted.

Column 40 Lines 34-35 in Claim 11 change:
11. The sleeping-posture-control bed system according to claim 7, further comprising a bed mat to be placed on the bed floor, the bed mat having a higher compressibility at a central portion in a [lateral direction] width of the bed mat than at both end portions in the [lateral direction] width of the bed mat.
To be:
11. The sleeping-posture-control bed system according to claim 7, further comprising a bed mat to be placed on the bed floor, the bed mat having a higher compressibility at a central portion in a width of the bed mat than at both end portions in the width of the bed mat.

Column 40 Lines 49 - Column 41 Lines 1-4 in Claim 14 change:

Signed and Sealed this  
Twenty-second Day of May, 2018

Andrei Iancu  
*Director of the United States Patent and Trademark Office*

14. A sleeping-posture-control bed system comprising:
   a bed floor including a back-lifting portion configured to lift a user's back, the back-lifting portion including a back-receiving surface and a head-receiving surface, each of the back-receiving surface and the head-receiving surface being capable of tilting upward and downward and being adjusted at different tilt angles;
   a bed-floor support body supporting the bed floor; and
   a back-lifting driver configured to tilt the back-receiving surface and the head-receiving surface within a range of satisfying Mathematical Formula (1) such that the user's posture is changed without increasing a pressure of blood flow into the user's head, $$0° < \theta x \leq \zeta°, -45° \leq \theta y < 0°, \text{ and } 0° \leq \theta x + \theta y \quad (1)$$

where
   θx is a tilt angle of the back-receiving surface lifted from 0° at which the back-receiving surface is in an unlifted position; and
   θy is a tilt angle of the head-receiving surface when the back-receiving surface is at the tilt angle of θx and an extended line of the back-receiving surface is referred to as 0°.

To be:

14. A sleeping-posture-control bed system comprising:
   a bed floor including a back-lifting portion configured to lift a user's back, the back-lifting portion including a back-receiving surface and a head-receiving surface, each of the back-receiving surface and the head-receiving surface being capable of tilting upward and downward and being adjusted at different tilt angles;
   a bed-floor support body supporting the bed floor; and
   a back-lifting driver configured to tilt the back-receiving surface and the head-receiving surface within a range of satisfying Mathematical Formula (1) such that the user's posture is changed without increasing a pressure of blood flow into the user's head, $$0° < \theta x \leq 70°, -45° \leq \theta y < 0°, \text{ and } 0° \leq \theta x + \theta y \quad (1)$$

where
   θx is a tilt angle of the back-receiving surface lifted from 0° at which the back-receiving surface is in an unlifted position; and
   θy is a tilt angle of the head-receiving surface when the back-receiving surface is at the tilt angle of θx and an extended line of the back-receiving surface is referred to as 0°.